United States Patent
Kido

(10) Patent No.: US 8,993,320 B2
(45) Date of Patent: Mar. 31, 2015

(54) CULTURE METHOD TO OBTAIN AND MAINTAIN A PURE OR ENRICHED POPULATION OF MAMMALIAN NEURAL STEM CELLS AND/OR NEURAL/PROGENITOR CELLS THAT ARE PRONE TO DIFFERENTIATE INTO OLIGODENDROCYTE-LINEAGE CELLS IN VITRO

(76) Inventor: Tsuneo Kido, Gaithersburg, MD (US)

( * ) Notice: Subject to any disclaimer, the term of this patent is extended or adjusted under 35 U.S.C. 154(b) by 33 days.

(21) Appl. No.: 13/349,089

(22) Filed: Jan. 12, 2012

(65) Prior Publication Data

US 2012/0177614 A1    Jul. 12, 2012

Related U.S. Application Data

(60) Provisional application No. 61/431,944, filed on Jan. 12, 2011, provisional application No. 61/558,527, filed on Nov. 11, 2011.

(51) Int. Cl.
*C12N 5/0797* (2010.01)
*C12N 5/079* (2010.01)

(52) U.S. Cl.
CPC ............ *C12N 5/0622* (2013.01); *C12N 5/0623* (2013.01); *C12N 2500/44* (2013.01); *C12N 2500/90* (2013.01); *C12N 2501/01* (2013.01); *C12N 2501/105* (2013.01); *C12N 2501/115* (2013.01); *C12N 2501/13* (2013.01); *C12N 2501/135* (2013.01); *C12N 2533/32* (2013.01)
USPC ........................................................ 435/368

(58) Field of Classification Search
None
See application file for complete search history.

(56) References Cited

U.S. PATENT DOCUMENTS

| 2009/0238801 | A1* | 9/2009 | Woodbury et al. | 424/93.7 |
| 2009/0291496 | A1* | 11/2009 | Racey et al. | 435/366 |
| 2010/0158878 | A1 | 6/2010 | Capela et al. | |
| 2010/0261274 | A1 | 10/2010 | Vodyanyk et al. | |

OTHER PUBLICATIONS

Areceli Espinosa de los Monteros, et al: "02A progenitor cells transplanted into the neonatal rat brain develop into oligodendrocytes but not astrocytes", Proc. Natl. Acad. Sci. USA, vol. 90, pp. 50-54, Jan. 1993.
Judith A Schwartzbaum, et al; "Allergy and inflammatory transcriptome is predominantly negatively corelated with CD133 expression in glioblastoma", Neuro-Oncology 12(4): 320-327; Advance Access publication Dec. 24, 2009.
International Search Report mailed May 15, 2012; Appln. No. PCT/IB2012/000030.

* cited by examiner

*Primary Examiner* — Allison Fox
*Assistant Examiner* — Yvonne Pyla
(74) *Attorney, Agent, or Firm* — Zareefa B. Flener; Flener IP Law

(57) ABSTRACT

An isolated expandable human neural stem or progenitor cell wherein the cell is a progenitor cells or stem cell, maintains its capability to differentiate into neurons, astrocytes, and oligodendrocytes, maintains its ability to differentiate into oligodendrocyte lineage cells efficiently throughout subsequent passages, and the cell expresses at least cell surface antigens CD133 and CD140α. Also provided is a method of in vitro culturing an expandable neural progenitor or stem cell isolated from a mammalian central nervous system, and the culture itself, wherein said cell maintains its capability to differentiate into neurons, astrocytes, and oligodendrocytes and its ability to differentiate into oligodendrocyte-lineage cells efficiently. In addition, a method of treating a condition caused by a loss of myelin or a loss of oligodendrocytes is provided as is a composition comprising an isolated expandable neural stem cell or one cultured by the methods of the invention.

26 Claims, 15 Drawing Sheets

| Cell type | Positive Markers | Negative Markers |
| --- | --- | --- |
| HFSC cell | CD133, Sox2, Nestin, CD9, NG2, CD140a (PDGF-R!), A2B5 (weak), O4 (weak), Olig2, PSA-NCAM | CD44, GFAP, Neurofilament |
| Neural stem cell | CD133, Nestin, Sox2, Integrin ß1/CD29, SSEA-1/LEX/CD15, CXCR4/CD184 | CD34, CD45, CD44 |
| Radial glia | GLAST, Vimentin, RC2, BLBP | |
| Neuronal-restricted precursor (NRP) | PSA-NCAM, CD56 | A2B5 |
| Glial-restricted precursor (GRP) | A2B5 | PSA-NCAM |
| Neuronal progenitor | PSA-NCAM, Beta III tublin, Nestin | A2B5 |
| Immature neuron | ß III tublin, Doublecortin | |
| Mature neuron | MAP2, Neurofilament, Tau | |
| Astrocyte progenitor | S100ß, CD44 | GFAP |
| Type-1 astrocyte | GFAP | A2B5 |
| Type-2 astrocyte | GFAP, A2B5 | |
| Oligodendrocyte Type-2 Astrocyte progenitor (O2A) | CD140a (PDGF-R!), Olig2, NG2, A2B5, GD3, O4 (weak), | CD133 |
| Pro-oligodendroblast | NG2, A2B5, GD3 (weak), O4, Sox10 | CD133, Sox2, GalC, CNPase, MBP, PLP |
| Immature oligodendrocyte | A2B5, O4 (strong), GalC, CNPase (2',3'-Cyclic-nucleotide 3'-phosphodiesterase) | MBP |
| Mature oligodendrocyte | MBP, CNPase, PLP | NG2, GalC |

FIG. 2

CULTURE METHOD TO OBTAIN AND MAINTAIN A PURE OR ENRICHED POPULATION OF MAMMALIAN NEURAL STEM CELLS AND/OR NEURAL/PROGENITOR CELLS THAT ARE PRONE TO DIFFERENTIATE INTO OLIGODENDROCYTE-LINEAGE CELLS IN VITRO

FIELD OF THE INVENTION

This invention relates generally to the field of cell biology of neural stem cells and neural progenitor cells. More specifically, this invention provides a pure or enriched population of mammalian neural stem cells and/or neural progenitor cells that are prone to differentiate into oligodendrocyte-lineage cells in vitro, suitable for use in biological research, drug screening and human therapy.

CROSS-REFERENCE TO RELATED APPLICATIONS

This application is related to U.S. provisional patent application No. 61/431,944 filed on Jan. 12, 2011 and 61/558,527 filed on Nov. 11, 2011.

STATEMENT REGARDING FEDERALLY SPONSORED RESEARCH OR DEVELOPMENT

Not Applicable.

BACKGROUND OF THE INVENTION

During development of the central nervous system, primitive, multipotent neural stem cells (NSC) proliferate, giving rise to transiently dividing progenitor cells that eventually differentiate into the various cell types that compose the adult brain. The adult central nervous system mainly consists of neurons and glial cells, which include astrocytes and oligodendrocytes. The progenitor cells for neurons, astrocytes and oligodendrocytes originate sequentially from neural stem cells in the developing brain (see FIG. 1). Neuronal progenitor cells form first and differentiate into many types of neurons. Astrocytes develop second and function to support neuron survival. Finally, oligodendrocyte progenitor cells start to appear and migrate throughout the central nervous system. They then differentiate into mature oligodendrocytes, which produce myelin necessary for proper neuronal function.

Since oligodendrocytes play an important role in supporting the central nervous system, a pure or enriched population of oligodendrocytes or their predecessor cells (i.e., oligodendrocyte pre-progenitor cells and/or oligodendrocyte progenitor cells) would be useful for cell therapies and regenerative medicine such as in the treatment of neurological disorders including congenital demyelinating diseases (for example, Krabbe disease or Pelizaeus-Merzbacher disease), spinal cord injury and other conditions that result from defects in the myelin sheath that insulates nerve cells. These cells also can be used for research and for identifying new drugs for the treatment of many neurological disorders such as multiple sclerosis and schizophrenia.

Mature oligodendrocytes do not proliferate and do not survive well in culture, and the ability to obtain oligodendrocytes directly from tissue samples in quantities sufficient for use in research or human therapy is extremely difficult. As a result, the use of oligodendrocytes for these purposes is hindered by the lack of availability of these cells.

One solution to this problem involves obtaining neural stem cells and/or neural progenitor cells from tissue, expanding the cells in culture to obtain a sufficiently large quantity of cells which can subsequently differentiate into oligodendrocytes. Differentiation can take place either in vitro or in vivo, such as in the case of transplantation. This would result in a large population of oligodendrocytes or their progenitors or pre-progenitors for use in research and human therapy.

However, scientists have struggled to identify culture conditions that permit long term culture and mass expansion of oligodendrocyte progenitors and/or pre-progenitors—particularly from humans or non-human primates—wherein the resulting expanded cell population is primarily comprised of cells that retain the ability to differentiate into oligodendrocytes.

Several scientists have reported obtaining oligodendrocyte progenitor cells from rats ((Raff et al, *J. Neurosci.*, 3:1289, 1983; Raff et al, *Nature.*, 303:390, 1983; Espinosa de los Monteros et al, *Proc. Natl. Acad. Sci. U.S.A.*, 90:50, 1993). These proliferative oligodendrocyte progenitors are known as O-2A progenitors because of their ability to differentiate in vitro into either oligodendrocytes or type 2 astrocytes. Other scientists have identified rat or mouse oligodendrocyte pre-progenitors in primary culture ((Gallo, Armstrong R C, *J. Neurosci.*, 15:394, 1995; Grinspan, Franceschini B, *J. Neurosci. Res.*, 41:540, 1995; Decker et al, *Mol. Cell. Neurosci.*, 16:422, 2000). These cells are thought to be precursors of oligodendrocyte progenitors and are expected to be more beneficial in cell therapy because of their superior migration capacity as compared to oligodendrocyte progenitors. Unfortunately, scientists have been unable to effectively expand these cells for long periods of time in vitro. In contrast, scientists have reported culturing O2A progenitors from rat optic nerve or spinal cord using B104 conditioned medium or growth factor combinations such as (i) platelet derived growth factor-AA (PDGF-AA) with basic fibroblast growth factor (bFGF or basic FGF) and neurotrophin-3 (NT-3), or (ii) PDGF-AA with ciliary neurotrophic factor (CNTF) and NT-3. However, no one has succeeded in mass expansion of these cell types from primate tissue using these growth factors.

Thus, it remains very difficult to obtain and expand a pure or enriched population of oligodendrocytes and/or their predecessor cells from mammals other than rat or mouse. It is particularly difficult to obtain and expand these cells from humans and non-human primates. Therefore, a great need exists for methods for generating pure or enriched populations of mammalian neural stem cells or progenitor cells which are prone to differentiate into oligodendrocyte-lineage cells in vitro.

BRIEF SUMMARY OF THE INVENTION

The present invention relates to an isolated expandable human neural cell wherein the cell is a progenitor cells or stem cell, wherein the cell maintains its capability to differentiate into neurons, astrocytes, and oligodendrocytes, wherein the cell maintains its ability to differentiate into oligodendrocyte lineage cells efficiently throughout subsequent passages, and wherein the cell expresses at least cell surface antigens CD133 and CD140α.

The present invention also relates to a method of in vitro culturing an expandable neural cell wherein the cell is a progenitor cell or stem cell isolated from a mammalian central nervous system wherein said cell maintains its capability to differentiate into neurons, astrocytes, and oligodendrocytes and its ability to differentiate into oligodendrocyte-lineage cells efficiently, wherein the method comprises isolating and dissociating at least one cell from a human fetal neural tissue; culturing the cell at a temperature of 37° C., in an atmosphere comprising 1-20% $O_2$, and 5% $CO_2$, and in a chemically defined serum-free culture medium, wherein the medium comprises at least 5 ng/ml PDGF-AA, at least 0.5 ng/ml bFGF, and at least 10 μM 1-thioglycerol; and passaging the cell to obtain the expandable human neural cell.

The present invention further relates to a method of treating a condition caused by a loss of myelin or a loss of oligodendrocytes comprising administering to a subject a therapeutically effective amount of a composition comprising an isolated expandable human neural cell which is able to maintain its capability to differentiate into neurons, astrocytes, and oligodendrocytes, wherein the cell maintains its ability to differentiate into oligodendrocyte lineage cells efficiently throughout subsequent passages, and wherein the cell expresses at least cell surface antigens CD133 and CD140α.

The present invention also relates to an in vitro culture comprising at least one isolated neural cell obtained from a mammalian central nervous system wherein the cell is submerged in chemically defined serum-free culture medium which has at least 5 ng/ml PDGF-AA,—at least 5 ng/ml bFGF, and at least 10 μM 1-thioglycerol.

The present invention moreover relates to a pharmaceutical neural stem cell composition comprising an isolated expandable human neural cell.

The present invention additionally relates to the use of a pharmaceutical neural stem cell composition in a medicament to treat a condition.

The present invention also relates to a method of in vitro culturing and expanding neural stem cells and/or neural progenitor cells isolated from a mammalian central nervous system wherein said cultured and expanded cells maintain their ability to differentiate into oligodendrocyte-lineage cells. The culture of cells in the present invention is an adhesion culture.

The present invention further relates to an isolated pure or enriched population of expanded mammalian neural stem cells and/or neural progenitor cells that are prone to differentiate into oligodendrocyte-lineage cells (i.e. O4-positive cells with spider web morphology as shown in FIG. 7 and FIG. 15) in vitro.

The present invention moreover relates to mammalian oligodendrocyte-lineage cells via in vitro expansion and differentiation from neural stem cells and/or neural progenitor cells isolated from mammalian central nervous system.

BRIEF DESCRIPTION OF THE DRAWINGS

FIG. 2 shows the comparison of marker expression of various CNS cells;

DETAILED DESCRIPTION OF THE DRAWINGS

Figure 1:
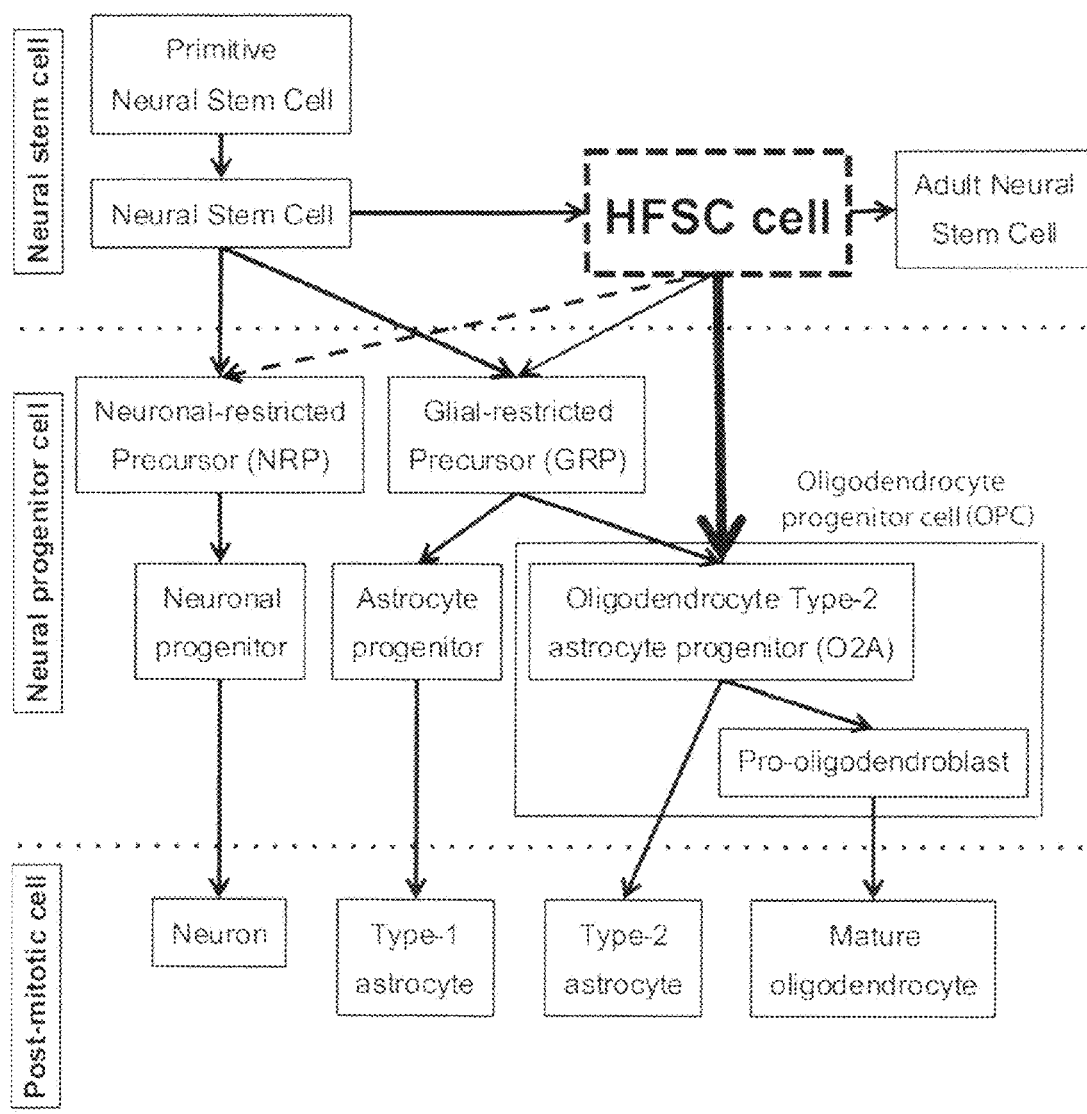
FIG. 1 depicts the development of neural stem cells and neural progenitor cells into the three main cell types in the brain-neurons, astrocytes and oligodendrocytes.

FIG. 1 depicts the development of neural stem cells and neural progenitor cells into the three main cell types in the brain-neurons, astrocytes and oligodendrocytes. Solid arrowed lines indicated the progression of one cell type to another. The dashed line from HFSC cell to neuronal-restricted precursors (NRP) indicates that the HFSC cell have a lower tendency to become neuronal fate. The heavy bolded line from the HFSC cell to the O2A cells indicates that the HFSC cell has a greater tendency to produce oligodendrocyte-lineage cells. The multi-potentiality of HFSC cell to differentiate into neuron, astrocyte and oligodendrocyte was shown in Example 7 (see FIG. 14). The tendency of HFSC cell to differentiate into oligodendrocyte-lineage cells was shown in Example 2 (see FIG. 7) and Example 8 (see FIG. 15).

FIG. 2 shows a comparison of marker expression of various CNS cells. This invention disclosed the phenotype of HFSC cell in Example 7 (see FIG. 12 and FIG. 13) and summarizes the same in this figure. As discussed later, a HFSC cell is not the same as any other cell type and has both features of neural stem cell and oligodendrocyte Type-2 Astrocyte progenitor (O2A).

Figure 3:
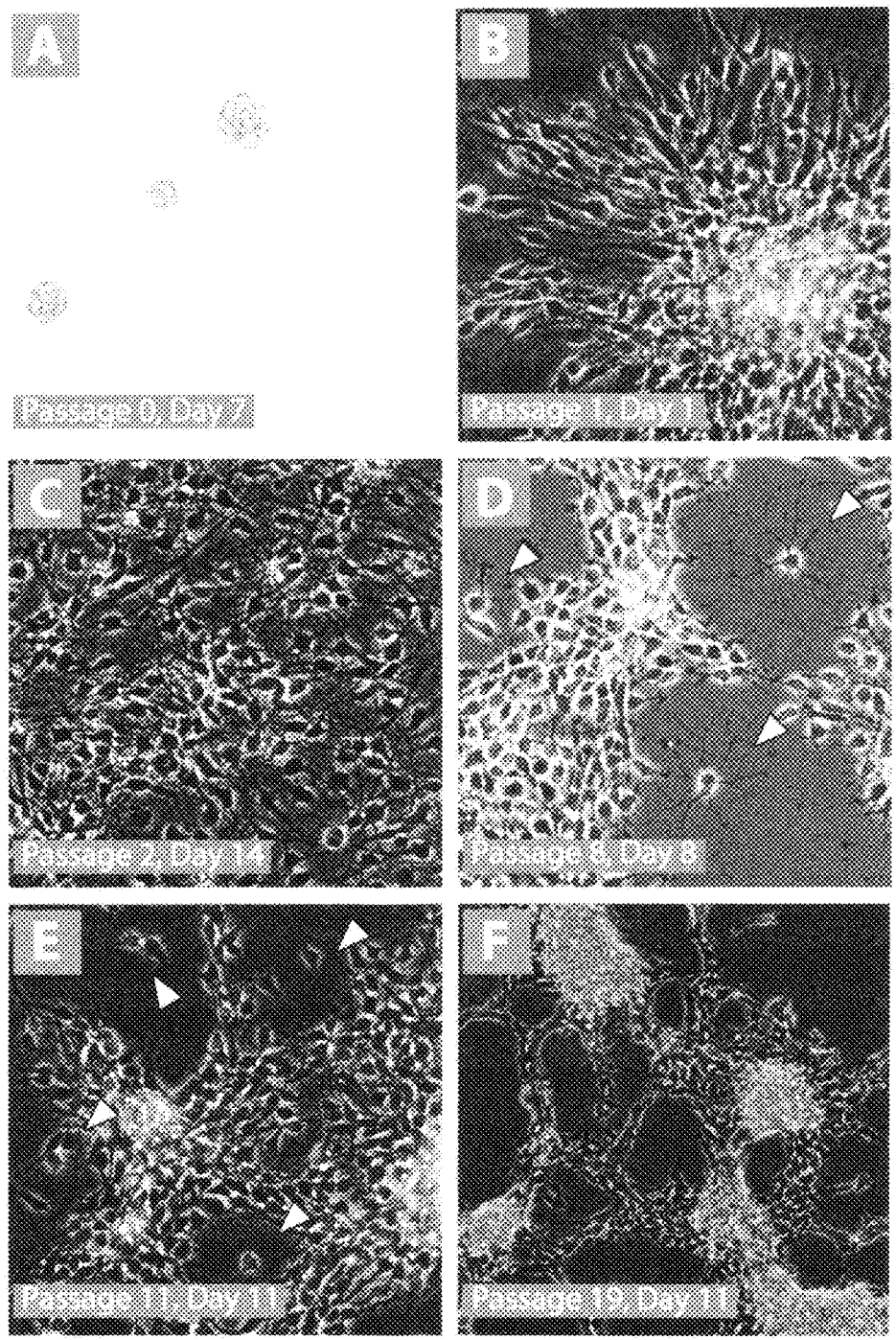
FIG. 3 depicts contrast images of Human Fetal Stem Cells (cell line #2b) in slides A-F.

FIG. 3 depicts contrast images of Human Fetal Stem Cells (cell line #2b) in slides A-F. FIG. 3, slide A is a phase contrast image taken with an inverted microscope showing HFSC cells (cell line #2b) cultured in DMEM/F12 containing glutamine and HEPES and supplemented with B27 supplement (Invitrogen™), non-essential amino acids (NEAA) (Invitrogen™), 1.5 mM pyruvate (Invitrogen™), 55 μM β-mercaptoethano (Invitrogen™), and 1 mM N-acetyl-L-cysteine (SIGMA-ALDRICH™), (in combination referred to as "HFSCM1 medium" hereinafter) with 20 ng/ml PDGF-AA and 10 ng/ml bFGF in an incubator maintained at 37° C., 5% $O_2$, and 5% $CO_2$ incubator. The cells shown are from passage 0, day 7. The cells formed spheres and these spheres were plated onto a poly-omithine coated culture plate directly without dissociating spheres at passage 1.

FIG. 3, slide B & slide C, are phase contrast images taken with an inverted microscope showing HFSC cells (cell line #2b) cultured as described in the description of FIG. 3, slide A hereinabove. The cells shown are from passage 1, day 1 and passage 2, day 14, respectively. The cells plated directly onto a poly-ornithine coated culture plate attached and spread out from spheres (FIG. 3, slide B). The passaged cells could expand successfully in this culture condition in subsequent passage (FIG. 3, slide C).

FIG. 3, slides D-F are phase contrast images taken with an inverted microscope showing HFSC cells (cell line #2b) after multiple passages and cultured in HFSCM1 medium with 100 ng/ml PDGF-AA, 10 ng/ml bFGF, 10 ng/ml IGF-1 and 50 μM 1-thioglycerol in an incubator maintained at 37° C., 5% $O_2$, and 5% $CO_2$ incubator. Most HFSC cells were phase dark cells clustering with surrounding cells. The scattered cells that separated from the clusters tended to differentiate spontaneously into process-bearing multipolar cells (so-called "spider's web-like" morphology) that is characteristic to pro-oligodendroblasts or immature oligodendrocyte (indicated by white arrowheads in FIG. 3, slides D & E) but their frequency of appearance was usually less than 1%. The cells shown in FIG. 3, slides D, E, and F are from passage 8, day 8, passage 11, day 11 and passage 19, day 11, respectively.

Figure 4:
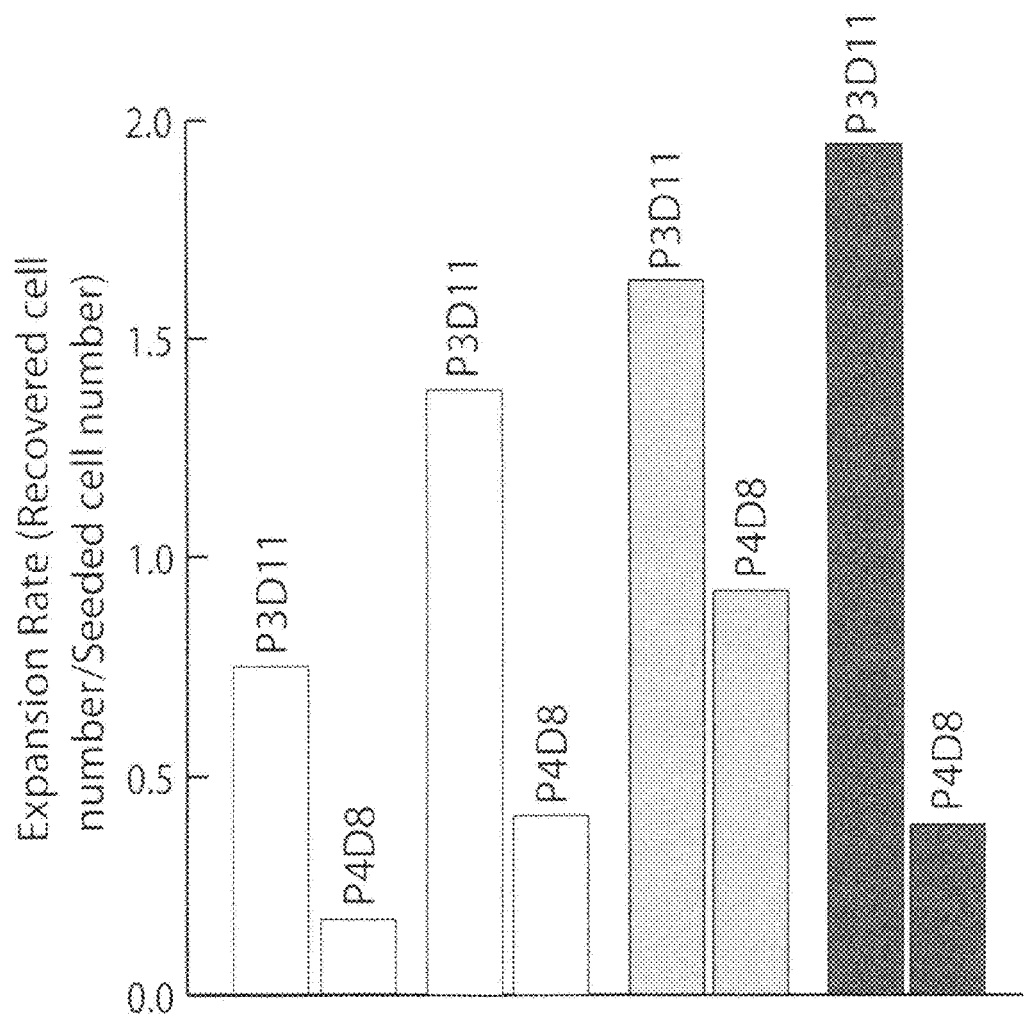
FIG. 4 illustrates the expansion rate of HFSC cells (cell line #2b) in the presence of different combinations of growth factors.

FIG. 4 illustrates the expansion rate of HFSC cells (cell line #2b) in the presence of different combinations of growth factors: (1): 20 ng/ml PDGF-AA+10 ng/ml bFGF; (2): 20 ng/ml PDGF-AA+10 ng/ml bFGF+5 ng/ml NT-3; (3): 20 ng/ml PDGF-AA+10 ng/ml bFGF+10 ng/ml IGF-1; (4): 20 ng/ml PDGF-AA+10 ng/ml bFGF+5 ng/ml NT-3+10 ng/ml IGF-1. The cells were harvested at day 11 of passage 3 (P3D11) and number of live cells in each condition was counted. Then, they were passaged in the same condition that was used at passage 3 at the same cell density. The cells were harvested at day 8 of passage 4 (P4D8) and number of live cells in each condition was counted (these cells were harvested before they became sub-confluent because they started forming spheres). Condition (4) was most effective at passage 3 but not at passage 4. Condition (3) was effective at both passages.

Figure 5:
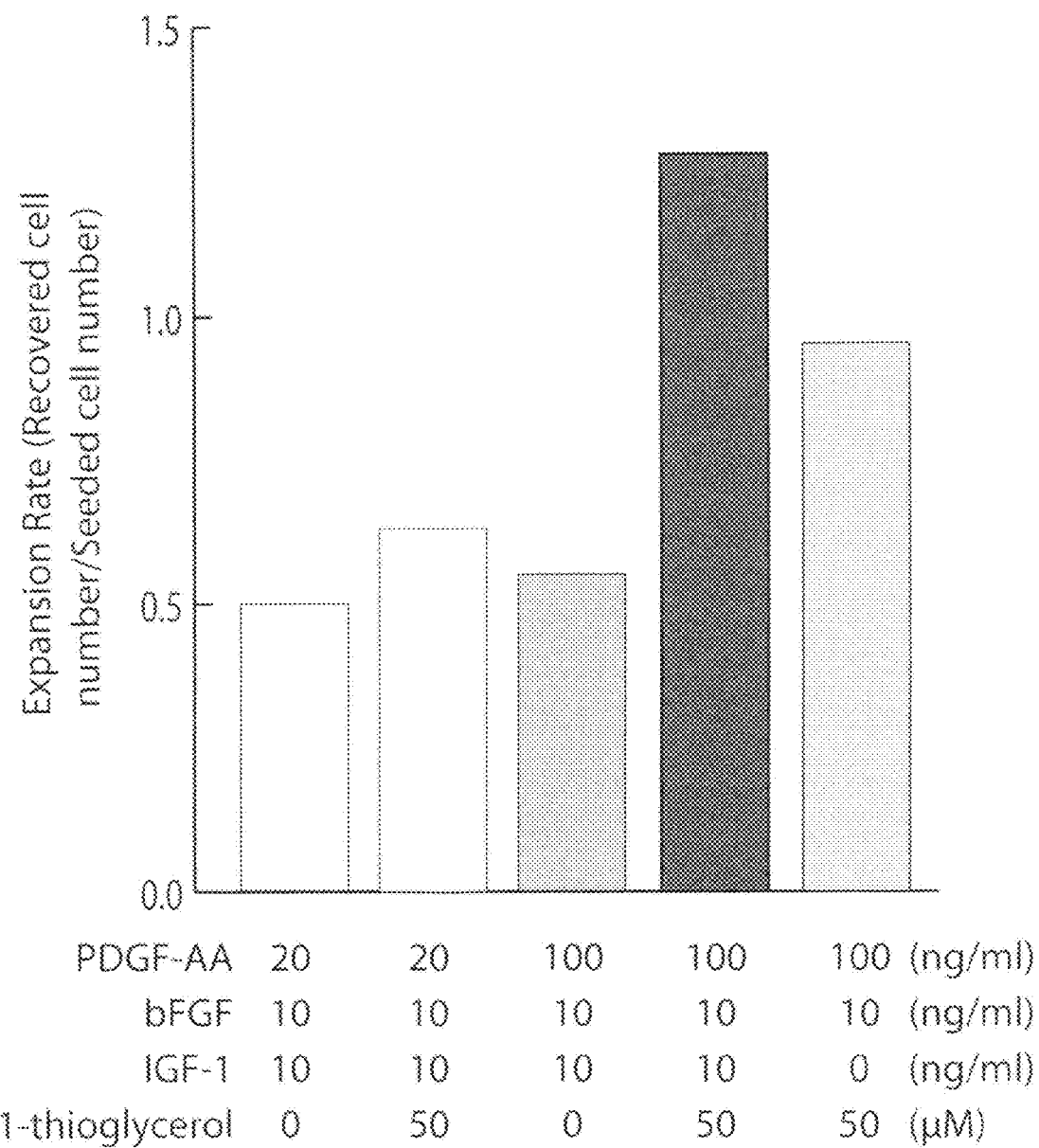
FIG. 5 illustrates the effects of high dose of PDGF-AA (100 ng/ml) and 1-thioglycerol on the proliferation of HFSC cells (cell line #2b)

FIG. 5 illustrates the effects of high dose of PDGF-AA (100 ng/ml) and 1-thioglycerol on the proliferation of HFSC cells (cell line #2b); cultured in HFSCM1 medium in the presence of the following combinations of growth factors: (1): 20 ng/ml PDGF-AA+10 ng/ml bFGF+10 ng/ml IGF-1; (2): 20 ng/ml PDGF-AA+10 ng/ml bFGF+10 ng/ml IGF-1+50 μM 1-thioglycerol; (3): 100 ng/ml PDGF-AA+10 ng/ml bFGF+10 ng/ml IGF-1; (4): 100 ng/ml PDGF-AA+10 ng/ml bFGF+10 ng/ml IGF-1+50 μM 1-thioglycerol; (5): 100 ng/ml PDGF-AA+10 ng/ml bFGF+50 μM 1-thioglycerol. The cells were harvested at day 7 of passage 5 (these cells were harvested before they became sub-confluent because they started forming spheres as they did at passage 4) and number of live cells in each condition was counted. The combination of 20 ng/ml PDGF-AA+10 ng/ml bFGF was also tested, but the recovered cell number was too low to evaluate (less than $1 \times 10^4$ cells which was under the countable range) and its data was eliminated from this figure. The condition (1) could expand cells at passage 3 but couldn't expand cells at passage 5. The addition of 50 μM 1-thioglycerol [condition (2)] or the increase of PDGF-AA concentration to 100 ng/ml [condition (3)] had a very little positive effect on expansion rate. When the addition of 50 μM 1-thioglycerol and the increase of PDGF-AA concentration to 100 ng/ml were combined [condition (4)], the cell expansion rate improved dramatically and the cells could be expanded successfully. When IGF-1 was eliminated from this condition [condition (5)], the expansion rate decreased to <1, indicating that IGF-1 also promoted HFSC cell proliferation and/or survival.

Figure 6:
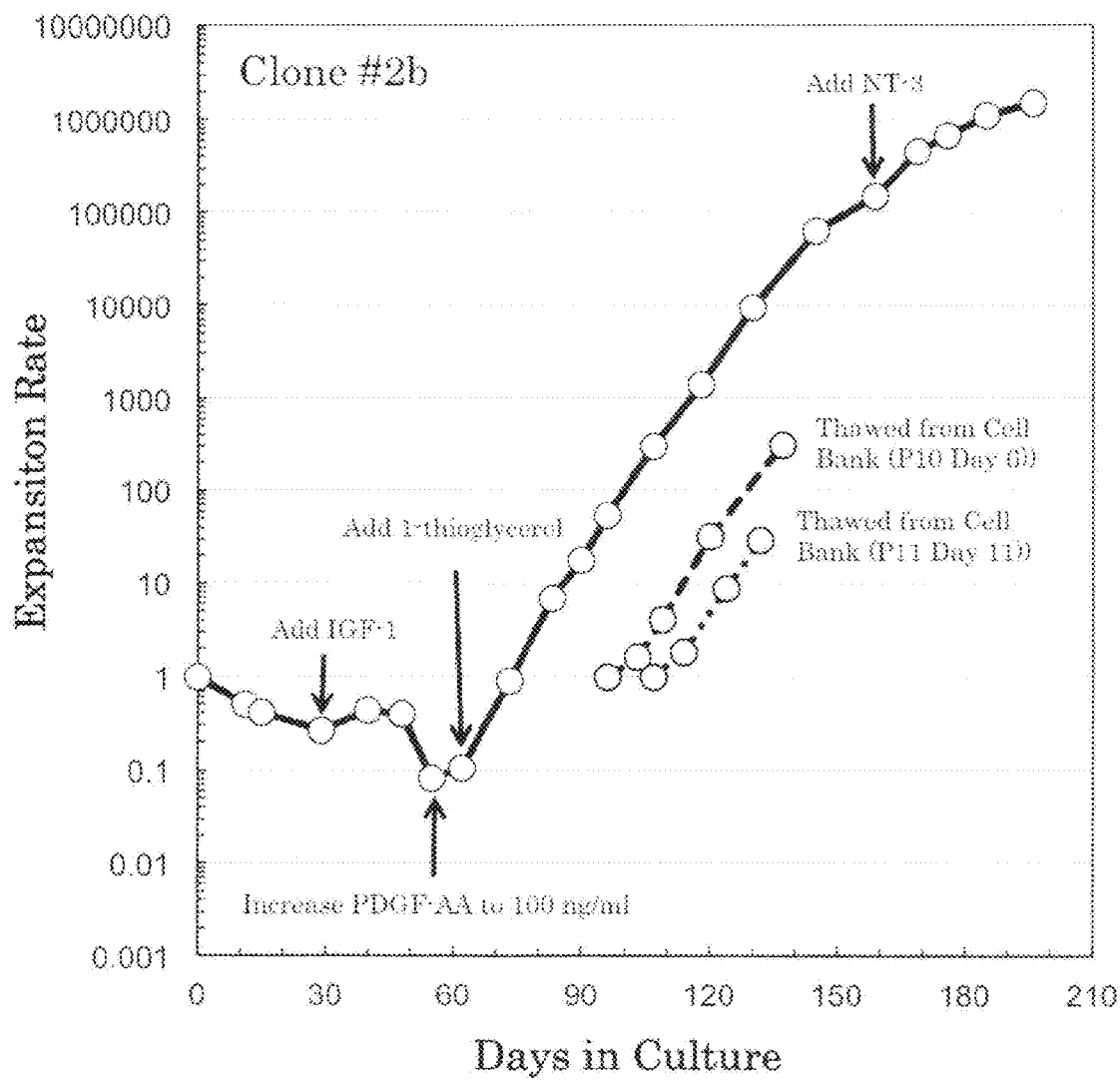
FIG. 6 illustrates a growth curve of HFSC cells (cell line #2b)

FIG. 6 shows a growth curve for a human HFSC cells (cell line #2b) (open circle with black line). HFSC cells (cell line #2b) were initially cultured in the presence of 10 ng/ml PDGF-AA and 10 ng/ml bFGF. 10 ng/ml IGF-1 was added from passage 3. The concentration of PDGF-AA was increased from 20 ng/ml to 100 ng/ml from passage 6. However, they have very little or no effects on the expansion rate of the cells. 50 μM 1-thioglycerol was added from passage 7. HFSC cells (cell line #2b) started to grow rapidly in the presence of 100 ng/ml PDGF-AA, 10 ng/ml bFGF, 10 ng/ml IGF-1 and 50 μM 1-thioglycerol. 10 ng/ml NT-3 was added at passage 17. NT-3 enhanced the cell growth a little bit but its effects disappeared after a passage. This panel also includes growth curves for human HFSC cells (cell line #2b) frozen at day 6 of passage 10 (P10 Day 6: open circle with dashed line) and day 11 of passage 11 (P11 Day 11: open circle with dot line). The frozen cells could be expanded at the similar speed after thawing.

Figure 7:
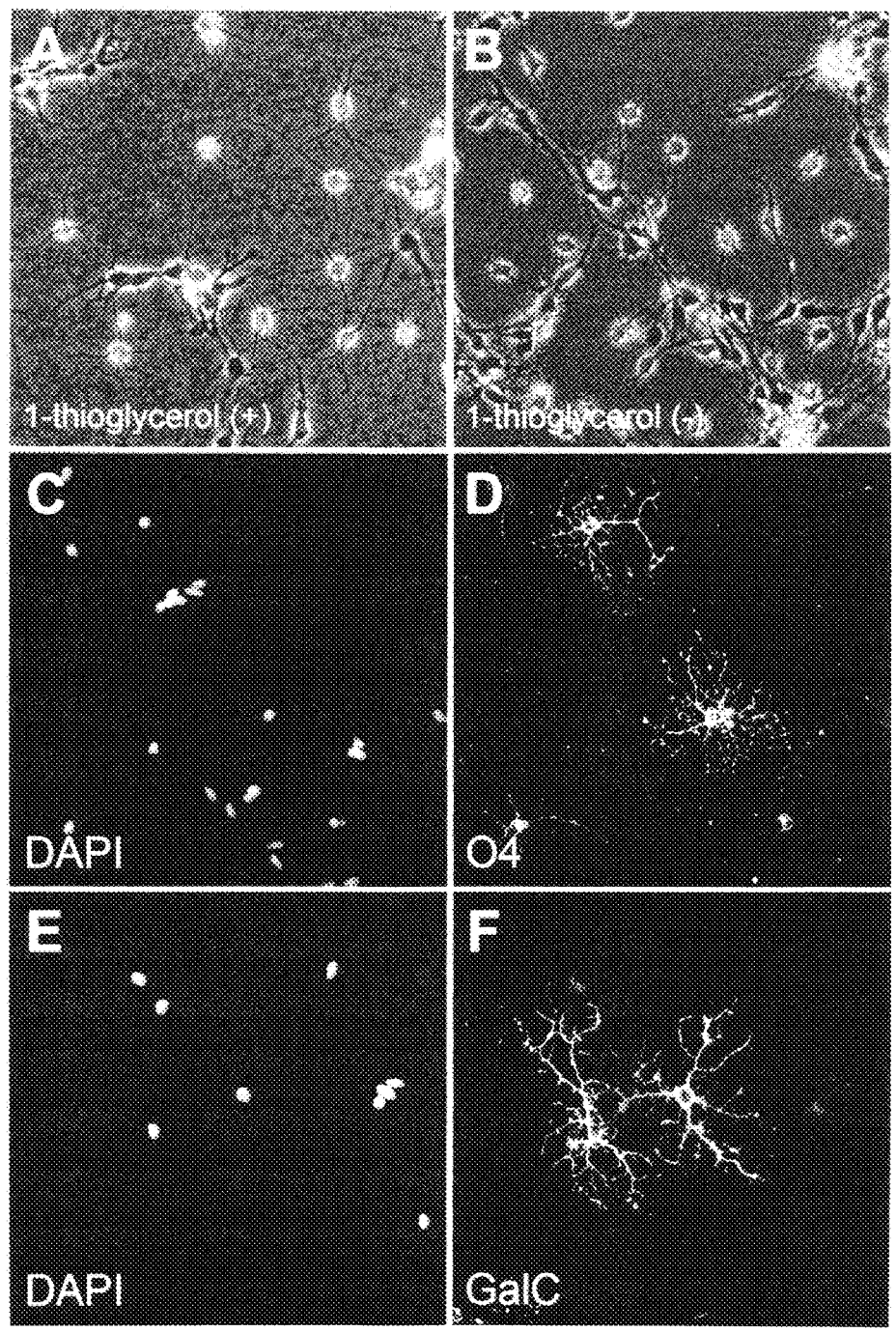
FIG. 7 depicts spontaneous differentiation of HFSC cells in serum-free medium in slides A-F.

FIG. 7 depicts spontaneous differentiation of HFSC cells in serum-free medium in slides A-F. Slides A and B are phase contrast images taken with an inverted microscope showing the morphological change of HFSC cells (cell line #2b) at passage 12, day 9 (FIG. 7, slides A & B) after being cultured in HFSCM1 medium supplemented with 20 ng/ml PDGF-AA, 10 ng/ml bFGF, 10 ng/ml IGF-1 and 50 μM 1-thioglycerol (FIG. 7, slide A) or without 1-thioglycerol (FIG. 7, slide B). HFSC cells were differentiated spontaneously without replenishing bFGF between changing medium. Even in the same condition, HFSC cells didn't differentiate if bFGF was replenished everyday and seemed to grow slowly. In addition, HFSC cells were blocked to differentiate and formed clusters when 40 ng/ml or higher PDGF-AA was used. By decreasing the PDGF-AA concentration from 100 ng/ml to 20 ng/ml and without replenishing bFGF, the cells could be differentiated spontaneously into process-bearing multipolar cells with spider's web-like morphology, which expressed the O4 antigen (FIG. 7, slides C & D) and/or GalC antigen (FIG. 7, slides E & F), a defining characteristic of oligodendrocyte-lineage cells [i.e., pro-oligodendroblast (O4-positive and GalC-negative), immature oligodendrocyte (O4-positive and GalC-positive)].

Figure 8:
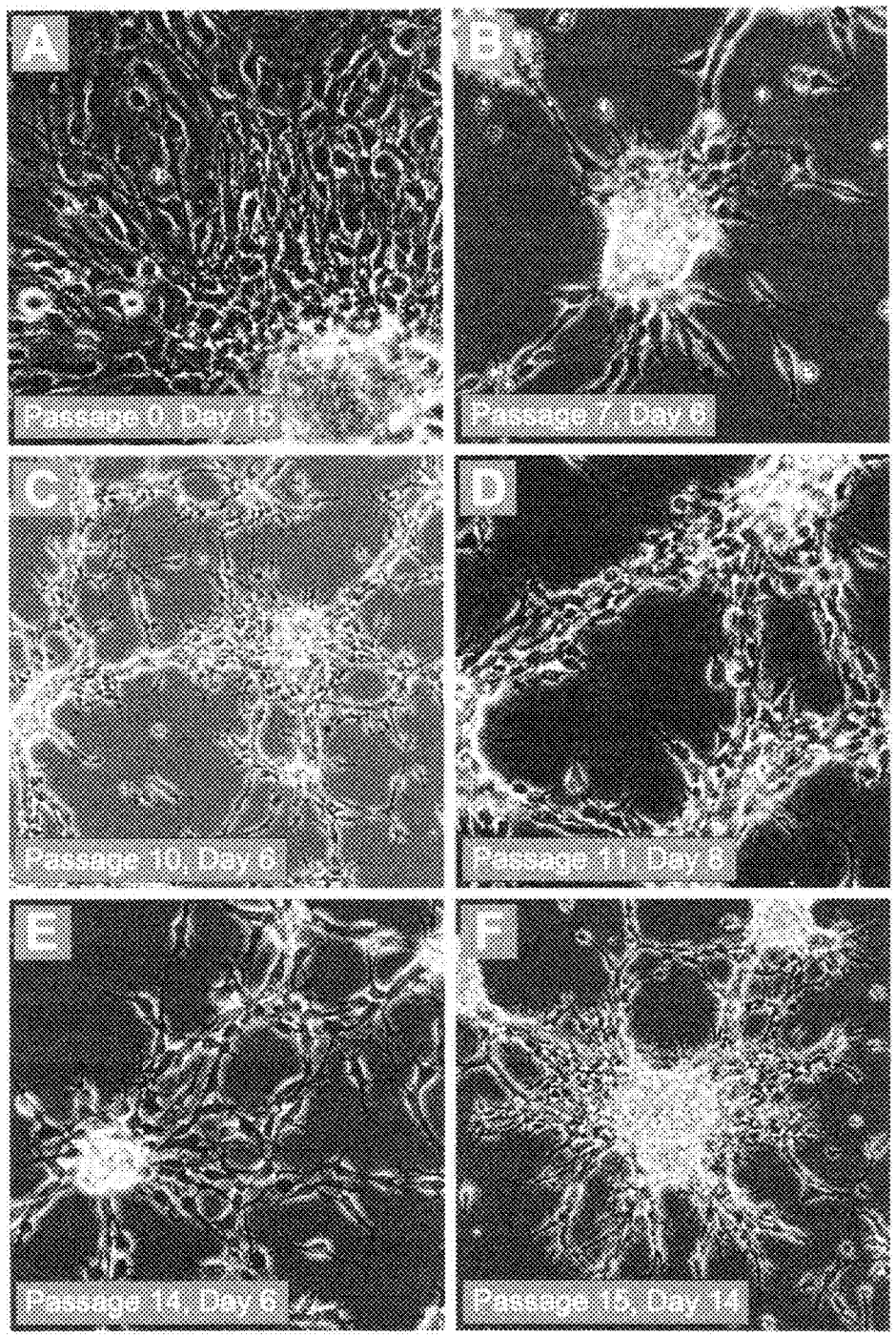
FIG. 8 is a phase contrast images taken with an inverted microscope showing the morphology of HFSC cells (cell line #3) at various passages.

FIG. 8 is a phase contrast images taken with an inverted microscope showing the morphology of HFSC cells (cell line #3) at various passages. The conventional neural stem cells were initially expanded in the presence of bFGF and EGF for 15 days (see FIG. 8, slide A at Day 15 of Passage 0). After that, the cells were cultured in the HFSCM1 medium with 20 ng/ml PDGF-AA and 10 ng/ml bFGF in an incubator maintained at 37° C., 5% $O_2$, and 5% $CO_2$ incubator. PDGF-AA concentration was increased to 100 ng/ml and 10 ng/ml of IGF-1 was added from passage 4 (see FIG. 9). 50 μM 1-thioglycerol was added from passage 8 (see FIG. 9). Their morphology became almost identical with cell line #2b after several passages.

Figure 9:
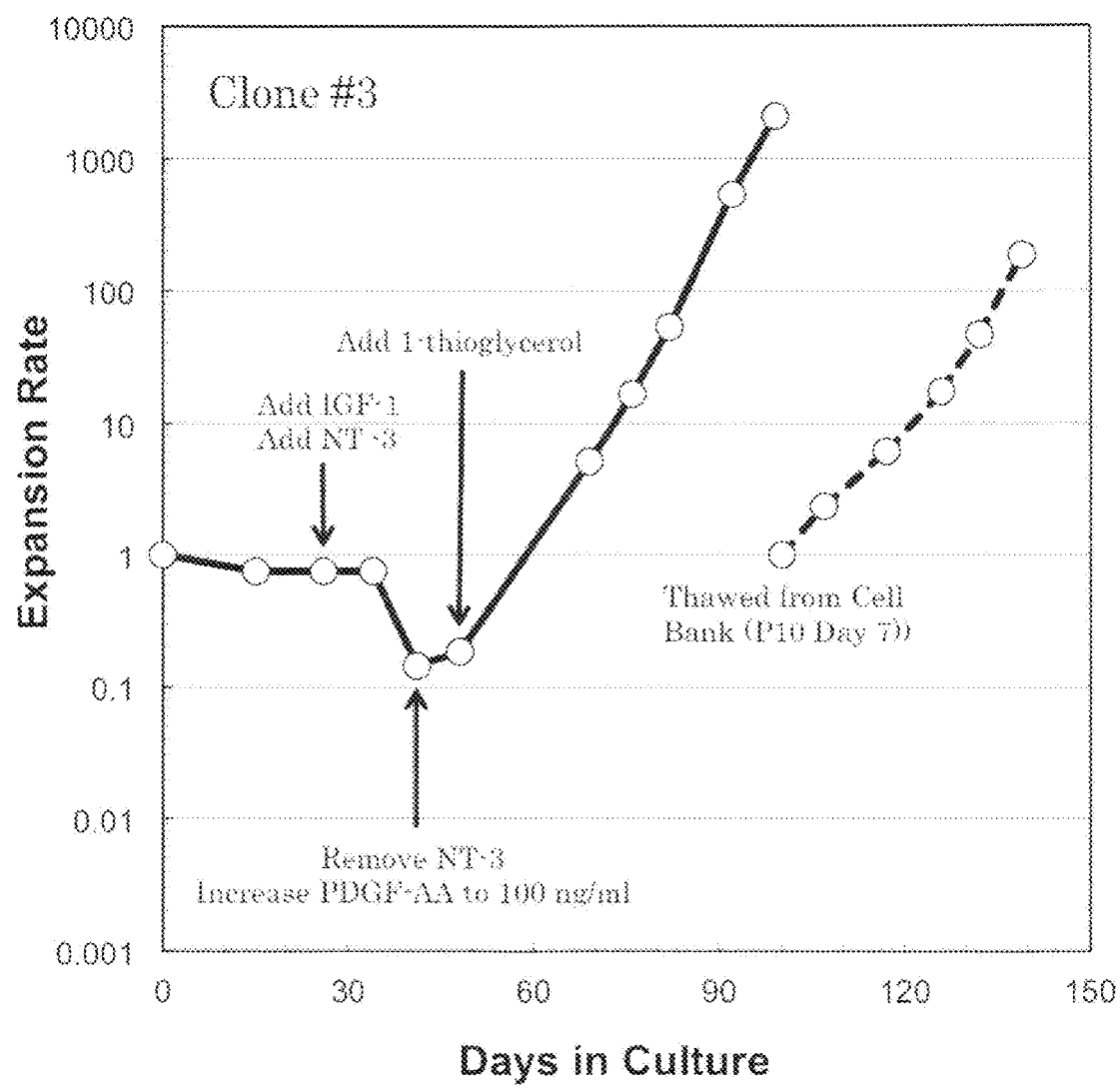
FIG. 9 illustrates a growth curve of HFSC cells (cell line #3)

FIG. 9 shows a growth curve for a human HFSC cells (cell line #3) (open circle with black line). HFSC cells (cell line #3) were initially cultured in the presence of 10 ng/ml EGF and 10 ng/ml bFGF to expand conventional neural stem cells. Then, the growth factor combination was changed to 20 ng/ml of PDGF-AA and 10 ng/ml bFGF from passage 1. 10 ng/ml IGF-1 and 10 ng/ml NT-3 were added from passage 2. Based on the data shown in FIG. 4, NT-3 was removed form this culture and the concentration of PDGF-AA was increased from 20 ng/ml to 100 ng/ml from passage 4. However, they have very little or no effects on the expansion rate of the cells as shown in cell line #2b. 50 μM 1-thioglycerol was added from passage 5, and then HFSC cells (cell line #3) started to grow rapidly in the presence of 100 ng/ml PDGF-AA, 10 ng/ml bFGF, 10 ng/ml IGF-1 and 50 μM 1-thioglycerol as HFSC cells (cell line #2b). This panel also includes growth curves for human HFSC cells (cell line #3) frozen at day 7 of passage 10 (P10 Day 7: open circle with dashed line). The frozen cells could be expanded at the similar speed after thawing.

Figure 10:
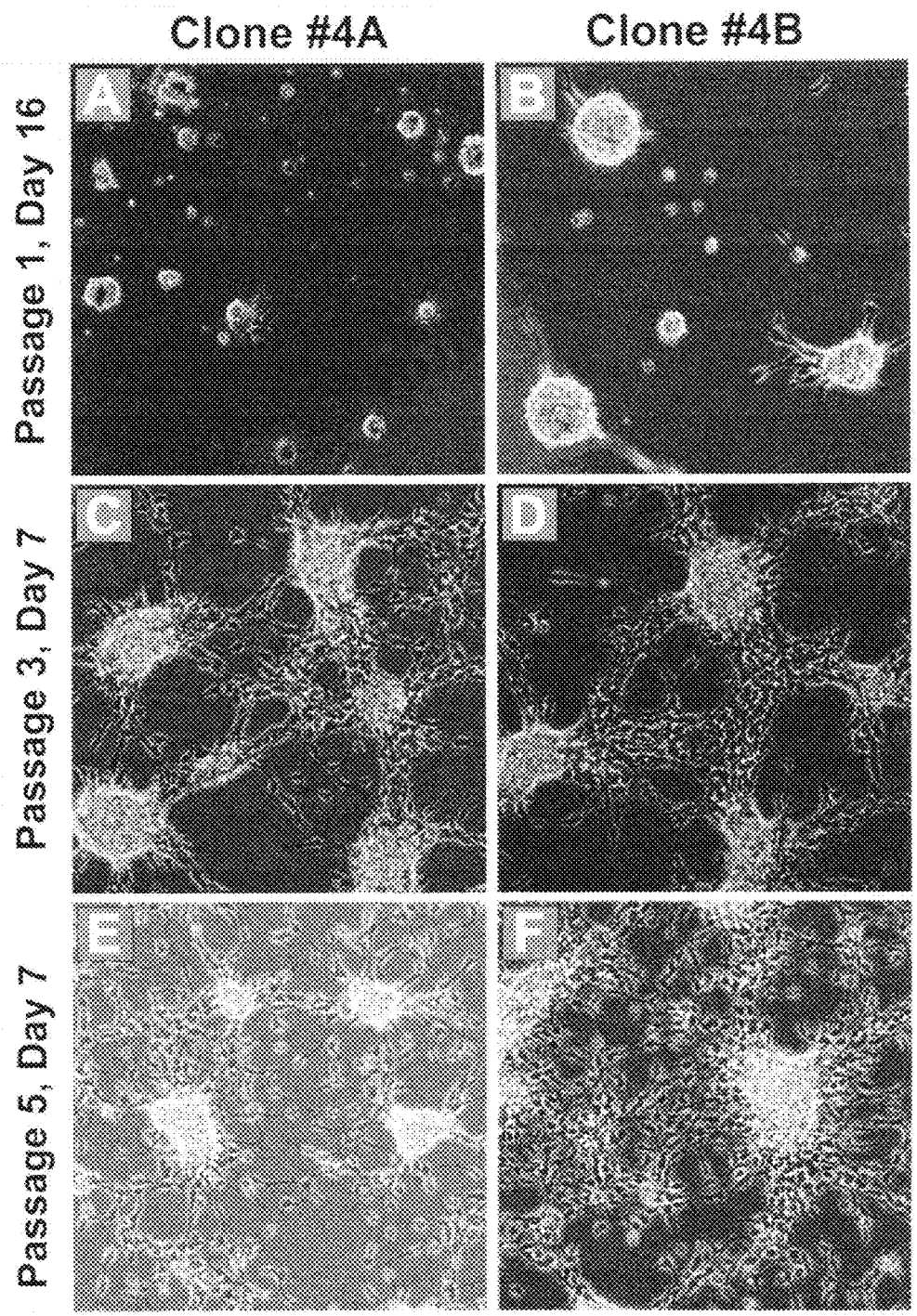
FIG. 10 is a phase contrast images taken with an inverted microscope showing the morphology of HFSC cells (cell line 4A and 4B) at various passages in slides A-F.

FIG. 10 is a phase contrast images taken with an inverted microscope showing the morphology of HFSC cells (cell line 4A and 4B) at various passages in slides A-F. The cells were cultured in the HFSCM1 medium and 50 µM 1-thioglycerol with 20 ng/ml PDGF-AA, 20 ng/ml bFGF and 20 ng/ml of IGF-1 (cell line #4A) or 100 ng/ml PDGF-AA, 20 ng/ml bFGF and 20 ng/ml of IGF-1 (cell line #4B) in an incubator maintained at 37° C., 5% $O_2$, and 5% $CO_2$ incubator. Cell line #4A grew slower than cell line #4B initially but started to grow at around the same speed as cell line #4B from passage 2. They became almost homogeneous and their morphology became almost identical with cell line #2b or #3 after 3 passages.

Figure 11:
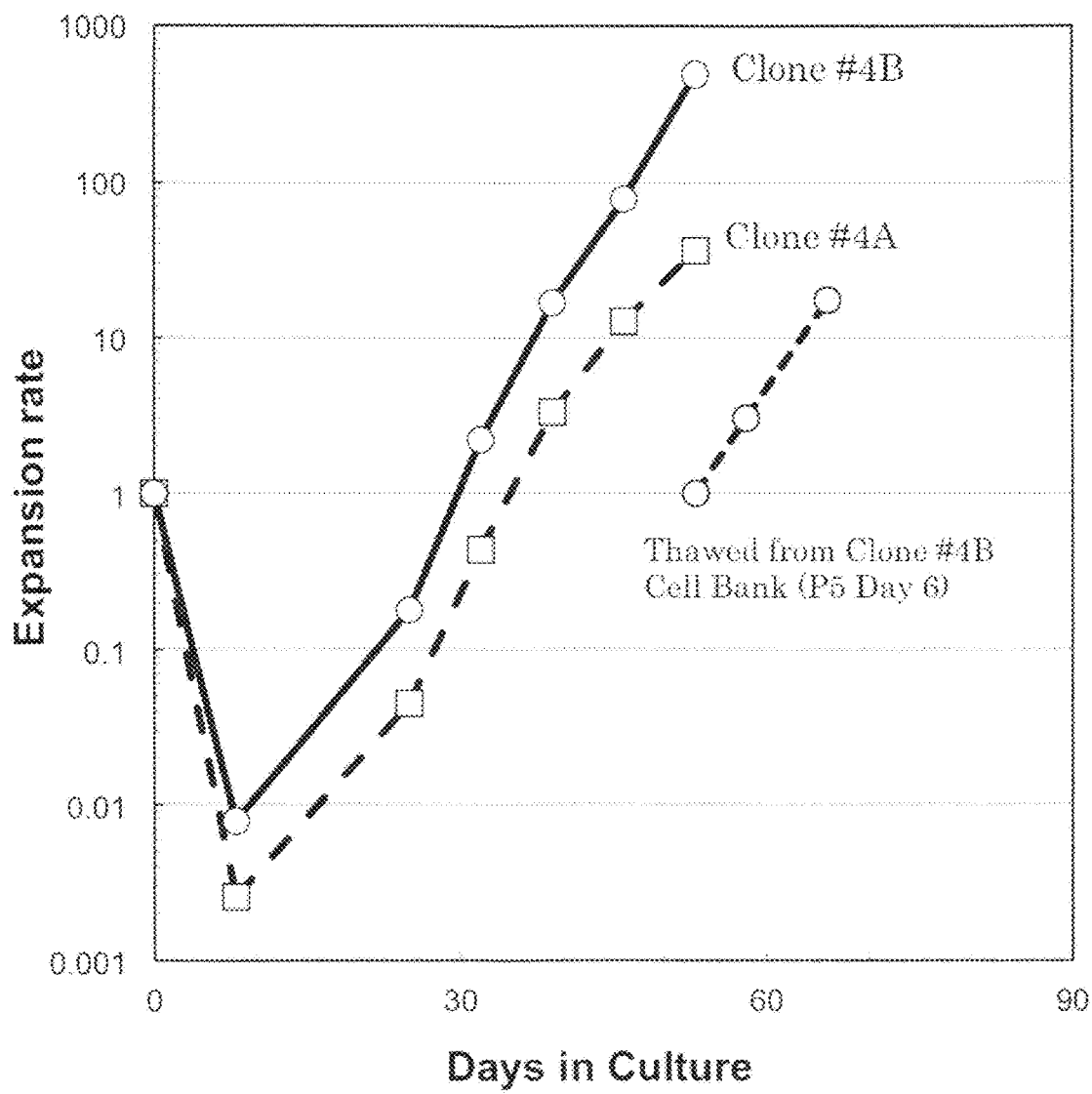
FIG. 11 illustrates a growth curve of HFSC cells (cell line #4A and #4B)

FIG. 11 shows a growth curve for a human HFSC cells (cell line #4A: open square with dashed line and #4B: open circle with black line). HFSC cells (cell line #4A) were cultured in the presence of 20 ng/ml of PDGF-AA, 20 ng/ml bFGF, 20 ng/ml, IGF-1 and 50 µM 1-thioglycerol. HFSC cells (cell line #4B) were cultured in the presence of 100 ng/ml of PDGF-AA, 20 ng/ml bFGF and 20 ng/ml IGF-1 and 50 µM 1-thioglycerol. The cell number of both cell lines was decreased dramatically at first and this decline was more prominent in cell line #4A. After this initial decline in cell number, they started to expand rapidly. This panel also includes a growth curve for human HFSC cells (cell line #4B) frozen at day 6 of passage 5 (P5 Day 6: open circle with dashed line).

Figure 12:
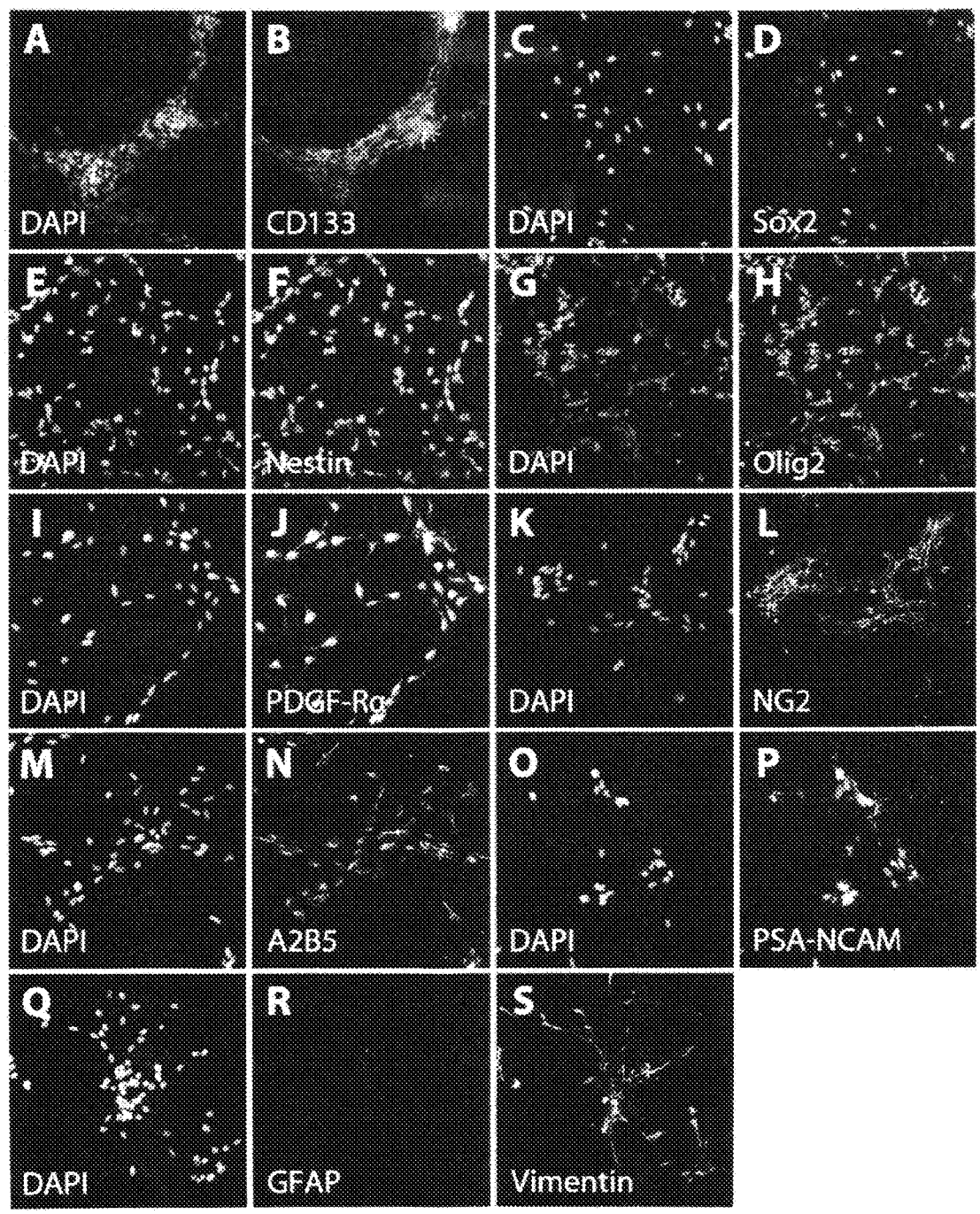
FIG. 12 illustrates the immuno-phenotype of undifferentiated HFSC cells in slides A-S.

FIG. 12 illustrates the immuno-phenotype of undifferentiated HFSC cells in slides A-S; (cell line #2b, passage 12-16) cultured in the presence of 100 ng/ml PDGF-AA, 10 ng/ml bFGF, 10 ng/ml IGF-1, and 50 µM 1-thioglycerol, and staining positive for either CD133, Sox2, Nestin, Olig2, PDGF-Rα, NG2, A2B5, PSA-NCAM, GFAP or Vimentin. DAPI was used to counterstain cell nuclei. These figures showed at least 90% of the cells were positive for CD133, Sox2, Nestin, Olig2, PDGF-Ra, NG2, A2B5 and vimentin but there were no GFAP-positive cells. The staining of PSA-NCAM was a little bit weak but still more than 90% of cells looked positive for PSA-NCAM.

Figure 13:
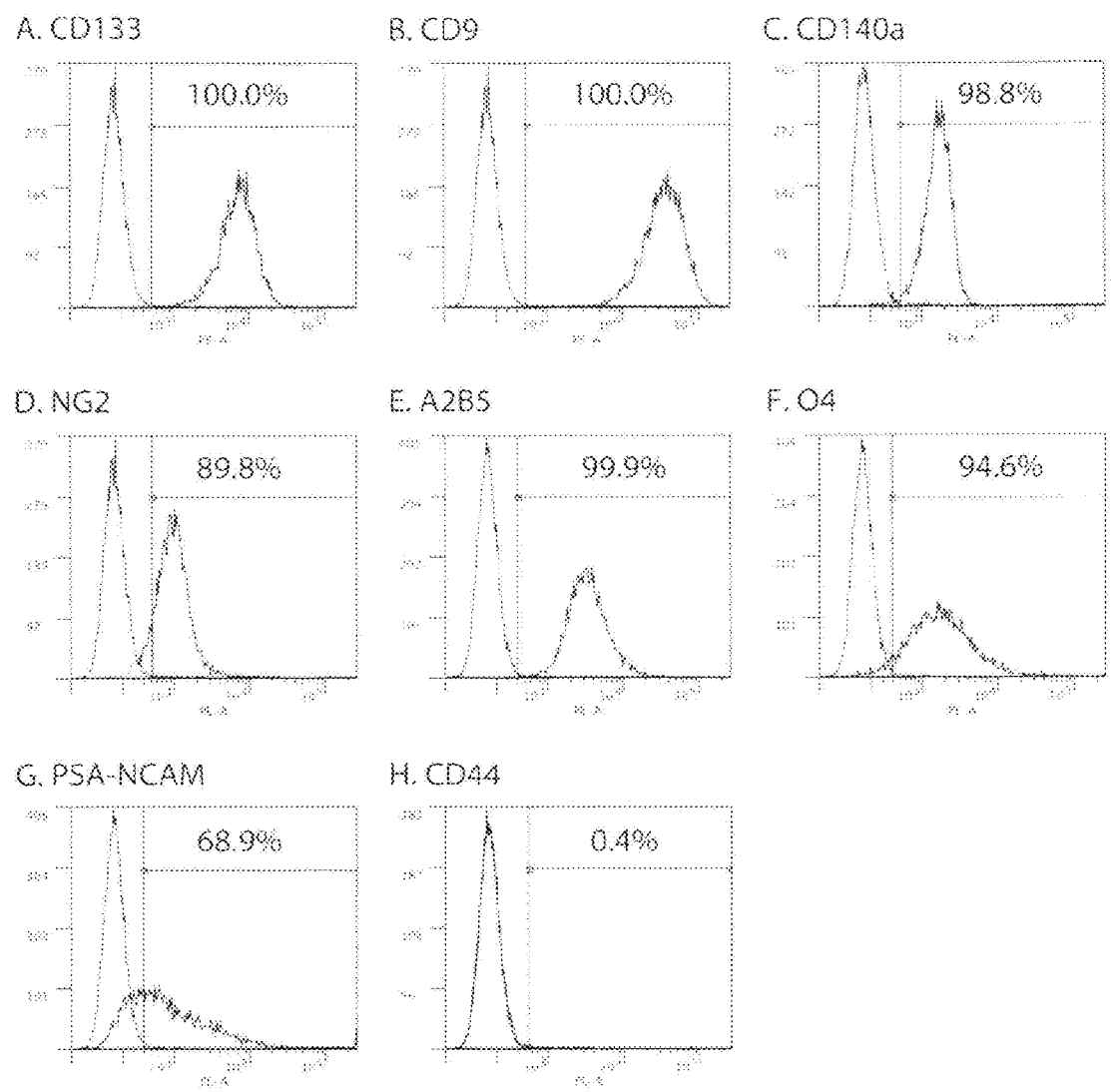
FIG. 13, in slides A-H, shows flow cytometry data illustrating the proportion of undifferentiated HFSC cells (cell line #2b, passage 13)

FIG. 13, in slides A-H, shows flow cytometry data illustrating the proportion of undifferentiated HFSC cells (cell line #2b, passage 13). Black line histograms represented the iso-type control and the gray-filled histograms represented each tested antigen. This data showed that most of HFSC cells were CD133-positive (FIG. 13, slide A), CD9-positive (FIG. 13 slide B), CD140a-positive (FIG. 13, slide C), NG2-positive (FIG. 13, slide D), A2B5 positive (FIG. 13, slide E), O4-positive (FIG. 13, slide F), and PSA-NCAM-positive (FIG. 13, slide G). As tested by an immunocytochemistry (data not shown), CD44 was negative (FIG. 13, slide H).

Figure 14:
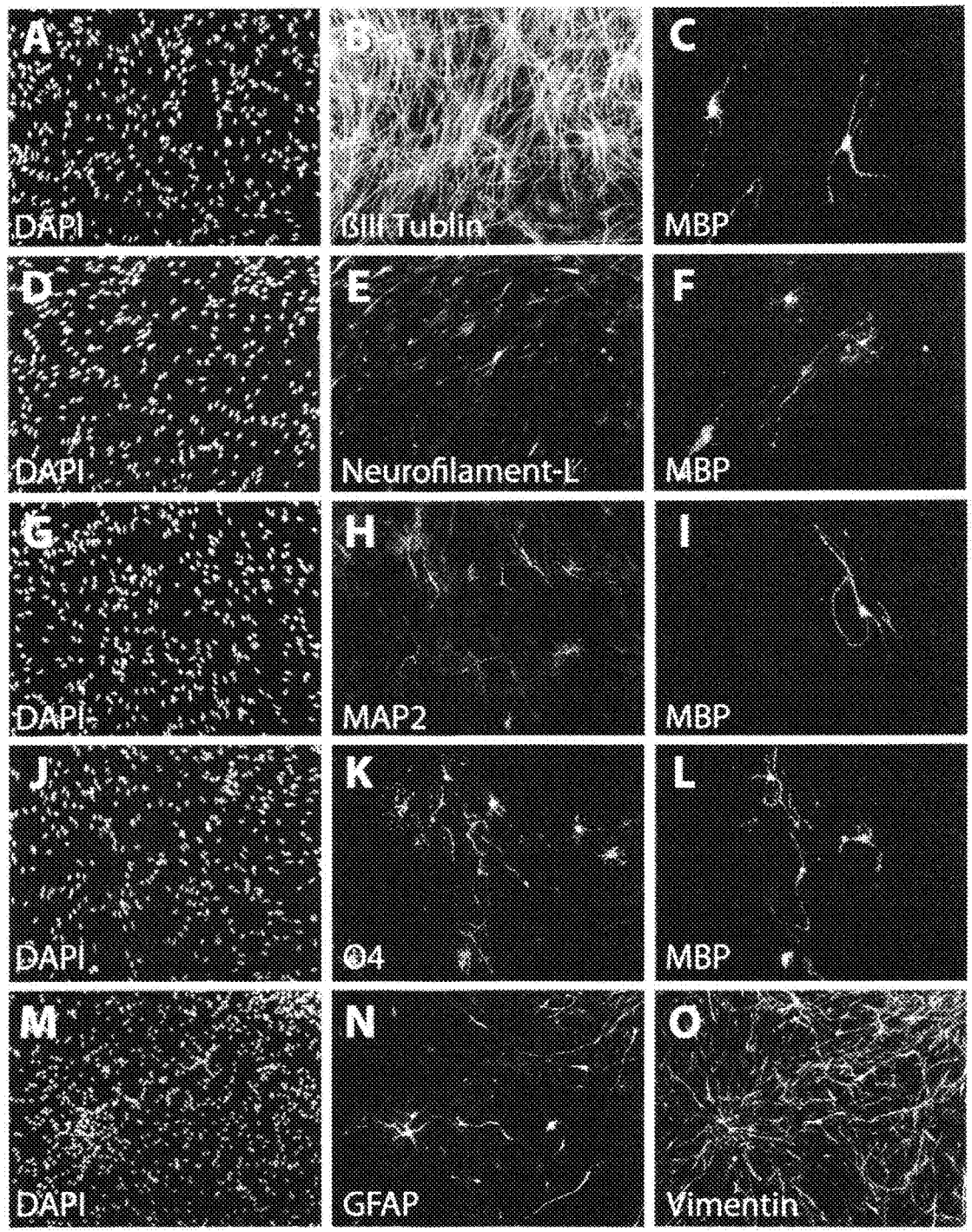
FIG. 14 illustrates the immuno-phenotype of differentiated HFSC cells (cell line #3, passage 15)

FIG. 14 illustrates the immuno-phenotype of differentiated HFSC cells (cell line #3, passage 15) cultured in serum-containing medium for 31 days and stained with antibodies that recognize neuron (βIII Tublin, Neurofilament-L, and MAP2), oligodendrocyte (O4, MBP) and astrocyte (GFAP) followed by a fluorescent secondary antibody. DAPI was used to counterstain cell nuclei. HFSC cell could differentiate into cells positive for each marker. To evaluate co-localization of neuronal axon and myelin, cells were co-stained with anti-βIII Tublin antibody and anti-MBP antibody (FIG. 14, slides A-C), anti-Neurofilament-L antibody and anti-MBP antibody (FIG. 14, slides D-F), anti-MAP2 antibody and anti-MBP antibody (FIG. 14, slides G-I). Only a few neuronal axon and myelin seemed to be co-localized. To evaluate co-localization of O4 antigen and MBP, cells were co-stained with O4 antibody and anti-MBP antibody (FIG. 14, slides J-L). Most signals for MBP were co-localized with signal for O4 antigen. HFSC cells could also differentiate into astrocyte that was positive for GFAP antigen (FIG. 14, slides M-O). In addition, many cells were positive for vimentin which was expressed in many epithelial cells including astrocyte and mesenchymal cells. Furthermore, undifferentiated cells were also positive for vimentin (data not shown).

Figure 15:
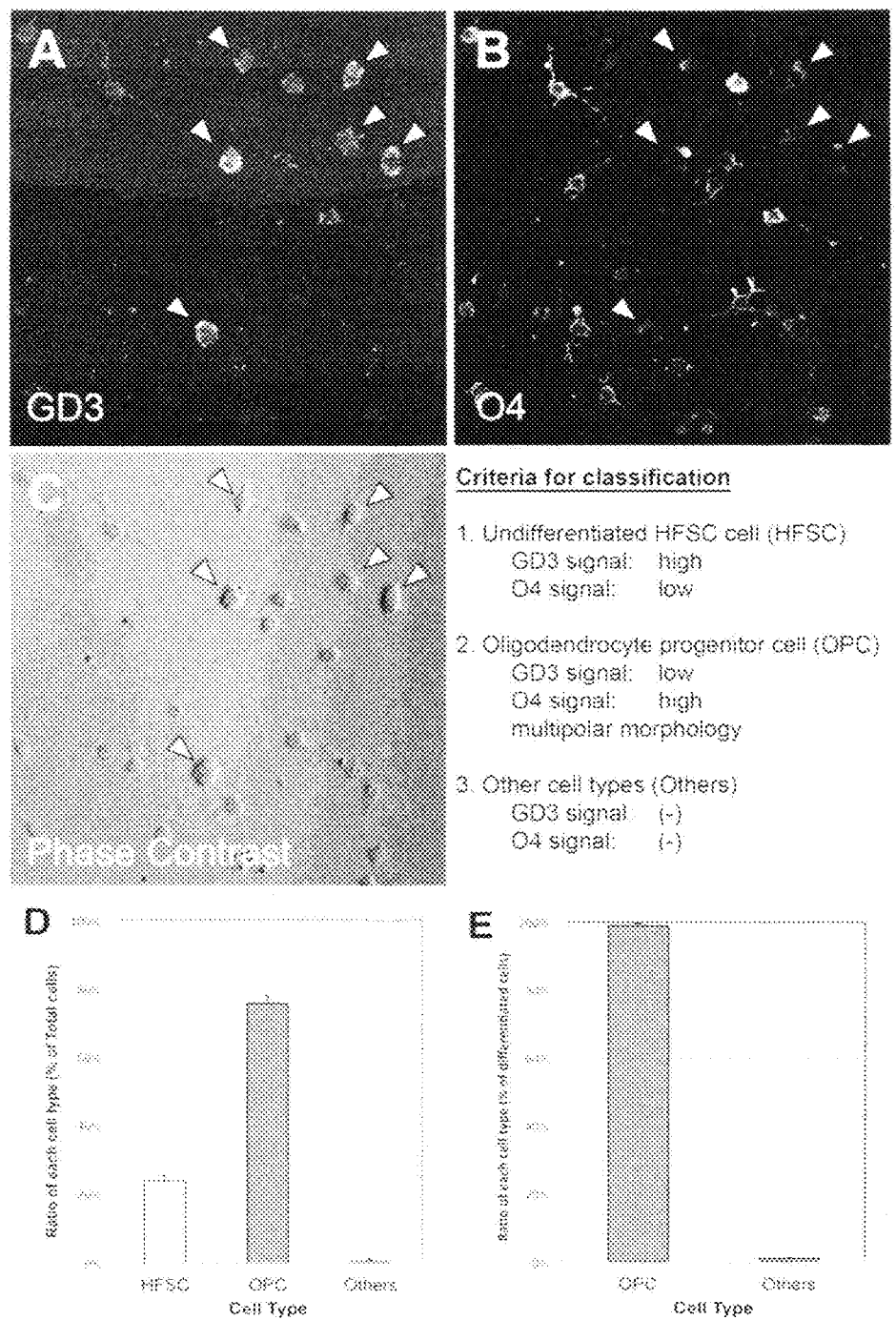
FIG. 15 illustrates the differentiation potential of HFSC cells (cell line #2b, passage 15) in slides A-E.

FIG. 15 illustrates the differentiation potential of HFSC cells (cell line #2b, passage 15) in slides A-E. The cells were differentiated in DMEM/F12 containing glutamine and HEPES and supplemented with B27 supplement, N2 supplement and 50 µM 1-thioglycerol with 10 ng/ml PDGF-AA, 100 ng/ml IGF-1, 10 ng/ml BDNF, and 100 µM pCPT-cAMP. The cells were stained with anti-GD3 antibody and O4 antibody following fluorescent secondary antibody after 4-day differentiation. Undifferentiated cells expressed GD3 stronger than oligodendrocyte progenitor cells and O4 vice versa (arrowhead of FIG. 15, slide A, B and C shows undifferentiated cells). The most of differentiated cell showed a multipolar morphology with weak GD3 signal and strong O4 signal, indicating they were oligodendrocyte progenitor cells or pro-oligodendroblast. Other cell types (e.g. astrocyte and neuron) were defined as a population of GD3-negative and O4-negative cells. FIG. 15, slide D shows the ratio of each cell population from 10 different images of the differentiated cells. More than 70% of total cells differentiated into oligodendrocyte progenitor cells (75.8%±2.09%). More than 20% of total cells were still undifferentiated cells (23.5%±2.03%). The other cell type were less than 1% of total cells (0.7%±0.41%). The ratio of oligodendrocyte progenitor cells and other cell types to differentiated cells (oligodendrocyte progenitor cells plus other cell types) were calculated and shown in FIG. 15, slide E. Oligodendrocyte progenitor cell was 99.1%±0.56% of differentiated cells whereas other cell types were 0.9%±0.56% of differentiated cells.

DETAILED DESCRIPTION OF THE PREFERRED EMBODIMENTS OF THE INVENTION

The present invention provides a method for culturing and expanding neural stem cells or neural progenitor cells isolated from a mammalian central nervous system to produce a pure or enriched population of neural stem cells or neural progenitor cells that have the ability to differentiate into oligodendrocytes or oligodendrocyte-lineage cells in vitro. Neural stem cells and neural progenitor cells both generate progeny that are either neuronal cells (such as neuronal progenitors or mature neurons) or glial cells including astrocytes and oligodendrocytes. While neural stem cells are self-renewable (i.e., able to proliferate indefinitely), neural progenitor cells may be, but are not necessarily, capable of self renewal. The culture methods of the present invention can produce an expanded cell population that can be differentiated into at least 70%, 80%, 90% or 95% oligodendrocyte-lineage cells, which are oligodendrocyte progenitor cells and oligodendrocytes, of differentiated cells.

The following abbreviations and definitions are used throughout this application:

The term "HFSC cell" or human fetal spinal cord-derived cell, refers to the pure or enriched population of expanded mammalian neural stem cells and/or neural progenitor cells that are described in this invention.

The term "HFSCM1 medium" refers to DMEM/F12 containing glutamine and HEPES and supplemented with B27 supplement (Invitrogen™), non-essential amino acids (NEAA) (Invitrogen™), 1.5 mM pyruvate (Invitrogen™), 55 µM β-mercaptoethanol (Invitrogen™), and 1 mM N-acetyl-L-cysteine (SIGMA-ALDRICH™) in combination.

The term "glial cells" refers to non-neuronal cells of the central nervous system and encompasses mature oligodendrocytes, astrocytes and committed progenitor cells for either or both of these cell types.

The term "multipotent progenitor cells" refers to neural progenitor cells that have the potential to give rise to cells from multiple, but a limited number of, lineages.

"Pluripotency" (derived from the Latin "plurimus" or "very many" and "potentia" or "powered") refers to a stem cell that has the potential to differentiate into any of the three germ layers: endoderm (interior stomach lining, gastrointestinal tract, the lungs), mesoderm (muscle, bone, blood, urogenital), or ectoderm (epidermal tissues and nervous system). Neural stem cells are multipotent and not pluripotent. Embryonic stem cells are pluripotent and not multipotent.

A "committed progenitor cell" is a progenitor cell that is committed, or destined, to become a specific type of mature cell. This is in contrast to a multipotent or a pluripotent progenitor cell, which has the potential to become one of two or more types of mature cells (such as O-2A progenitor cells which can become either oligodendrocytes or type-2 astrocytes, depending on timing and environmental factors).

An "oligodendrocyte" is a type of glial cell whose main function is to insulate nerve cell axons in the central nervous system of some vertebrates.

The term "oligodendrocyte-lineage cells" refers to oligodendrocytes, pro-oligodendroblast and oligodendrocyte progenitors (e.g. O2A progenitor). This term does not include glial-restricted precursors or neural stem cells.

The terms "oligodendrocyte progenitor cells" and "oligodendrocyte progenitors" are used interchangeably throughout this application and refer to cells that are committed to forming more progenitor cells and/or progeny that are oligodendrocytes in preference to neurons or non-neurological tissue. Unless otherwise specified, they may, but do not necessarily, have the capability of making other types of glial cells (such as type-2 astrocytes). This term as used herein does not encompass oligodendrocyte pre-progenitors or glial-restricted precursors (see FIG. 1).

"Oligodendrocyte pre-progenitors" are predecessor cells of oligodendrocyte progenitors.

"Pro-oligodendroblasts" are predecessor cells to post-mitotic oligodendrocytes.

"Expanding" cells in culture means to increase cell number in the presence of culture medium containing supplements which stimulate cell proliferation.

The cell "expansion rate" refers to the cell number on a particular date divided by the initial cell number at the start of culture.

"Expanded" neural progenitor cells or neural stem cells as used herein refers to neural progenitor cells or neural stem cells that are derived from isolated neural progenitor cells or neural stem cells that have proliferated in vitro, producing the expanded cell population.

"Passaging" cells (also known as "subculturing" or "splitting" cells) refers to a technique that enables cells to be kept alive and growing under laboratory culture conditions for extended periods of time by dissociating cells from one another (with enzymes like trypsin or collagenase and then transferring a small number of cells into a new culture vessel. Cells can be cultured for a longer time if they are passaged at regular intervals, as it avoids the premature senescence associated with prolonged high cell density.

A "growth environment" is an environment in which the cells of interest will proliferate, differentiate and/or mature in vitro. Features of the environment include the medium in which the cells are cultured, any growth factors or differentiation-inducing factors that may be present, and a supporting structure (such as a substrate on a solid surface) if present.

General Techniques

General methods in cell biology, protein chemistry, and antibody techniques can be found in Current Protocols in Protein Science (J. E. Colligan et al., eds., Wiley & Sons); Current Protocols in Cell Biology (J. S. Bonifacino et al., Wiley & Sons) and Current Protocols in Immunology (J. E. Colligan et al. eds., Wiley & Sons). Cell culture methods are described generally in the current edition of Culture of Animal Cells: A Manual of Basic Technique (R. I. Freshney etl, Wily & Sons); General Techniques of Cell Culture (M. A. Harrison & I. F. Rae, Cambridge Univ. Press). Tissue Culture supplies and reagents are available from commercial vendors such as Chemicon®, Millipore®, R&D Systems®, Invitrogen™, Nalgene-Nunc™ International, Sigma-Aldrich™, and SCIENCELL™ Research Laboratories.

Specialized reference books relevant to this disclosure include Principles of Neuroscience, $4^{th}$ edition, Kandel et al. eds., McGraw-Hill 2000; CNS Regeneration: Basic Science and Clinical Advances, M. H. Tuszynski & J. H Kordower, eds., Academic Press, 1999; The Neuron: Cell and Molecular Biology, 3 rd edition, I. B. Levitan and L. K. Kaczmarek, Oxford U. Press, 2001; Glial Cells: Their Role in Behavior, P. R. Laming et al. eds., Cambridge U. Press 1998; The Functional Roles of Glial Cells in Health and Disease, Matsas & Tsacopoulos eds., Plenum Pub. Corp, 1999: Glial Cell Development, Jessen & Richardson eds., Oxford U. Press, 2001; and Man of Steel, Adrian Hill, 1996.

In the context of cell ontogeny, the adjective "differentiated" is a relative term. A differentiated cell is a cell that has progressed further along the developmental pathway than the cell to which it is being compared. Thus, neural stem cells can differentiate to lineage-restricted progenitors. These, in turn, can differentiate into cells further along the pathway or to end-stage differentiated cells, such as mature neurons or oligodendrocytes.

Differentiated cells of this invention can be characterized according to whether they express phenotypic markers characteristic of oligodendrocytes. Classic immunocytochemical markers for these cells that may be present depending on the maturity of the cell population are the following:

Sox2: a marker for pluripotent stem cells and neural stem cells.

Nestin: a marker for neural stem cells.

CD133: a cell surface marker for neural stem cells.

PDGF-Receptor alpha (PDGF-Rα): the α chain of the platelet-derived growth factor receptor. A marker for oligodendrocytes and their progenitors.

CD140a: the same as PDGF-Rα. CD140a antibody recognizes an extracellular domain of PDGF-Rα. A cell surface marker for oligodendrocytes and their progenitors.

CD9: a cell surface glycoprotein that is know to complex with integrins and other transmembrane 4 superfamily proteins. A cell surface marker for germline stem cell, neural stem cell, oligodendrocyte, and mesenchymal stem cell.

PSA-NCAM: polysialylated-neural cell adhesion molecules. A cell surface marker for neuronal-restricted precursor (NRP), neuronal progenitor, neuroblast, and oligodendrocyte pre-progenitor. This marker is negative in glial-restricted precursor (GRP).

A2B5: a cell surface marker for glial-restricted precursor (GRP), glial progenitor cells and oligodendrocyte progenitor cell (OPC) and type 2 astrocytes. This cell surface marker is negative in neuronal-restricted precursor (NRP).

NG2: a chondroitin sulfate proteoglycan. A cell surface marker for macrophages and oligodendrocyte progenitor cells.

GD3: Ganglioside GD3. A marker for oligodendrocyte pre-progenitor and oligodendrocyte progenitors O4: a marker for oligodendrocytes and their progenitors.

Galactocerebroside C (GalC): a marker for immature oligodendrocytes.

Myelin basic protein (MBP): a marker for mature oligodendrocyte.

CD44: a cell-surface glycoprotein involved in cell-cell interactions, cell adhesion and migration and a receptor for hyaluronic acid. A cell surface marker for some epithelial cells and astrocyte lineage cells.

Glial fibrillary acidic protein (GFAP): a marker for astrocytes.

βIII Tublin: a marker for neuronal progenitors and neurons.

Neurofilament-L: a marker for mature neurons.

Microtubule-associated protein 2 (MAP2): a marker for mature neurons.

Tissue specific markers can be detected using any suitable immunological technique, such as flow immunocytochemistry for cell surface markers, or immunohistochemistry (for example, of fixed cells or tissue sections) for intracellular or cell-surface markers. A detailed method for flow cytometry analysis is provided in Gallacher et al, *Blood.*, 96:1740, 2000. Expression of a cell-surface antigen is defined as positive if a significantly detectable amount of antibody will bind to the antigen in a standard immunocytochemistry or flow cytometry assay, optionally after fixation of the cells, and optionally using a labeled secondary antibody or other conjugate to amplify labeling. To facilitate use in research or therapy, it is often beneficial to maximize the proportion of cells in the population that have the characteristics of oligodendrocytes or their progenitors. It is possible to obtain populations of cells that are at least 50%, 60%, 70%, 90% or 95% specific lineage cells, identified as being positive for one or more of the phenotypic markers characteristic of such cells.

For therapeutic applications relating to reconstitution of neural function, it is often desirable to minimize the ability of the cell population to form other cell types, particularly undifferentiated stem cells, and cells of non-ectodermal lineage. Depending on the application, it may also be advantageous to minimize the proportion of cells of the neuronal lineage and their committed progenitors or cells of the astrocyte lineage and their committed progenitors. The contamination of the populations according to this invention have less than 30%, 20%, 10% or 5% contamination with these other types of cells.

The methods of the present invention cannot result in the development of an entire human organism.

The method of the present invention involves culturing isolated neural stem cells and/or neural progenitor cells from a mammalian central nervous system in a defined medium that permits the expansion of the cells through multiple passages. The cells cultured using the method of the present invention retain their ability, throughout expansion, to differentiate into oligodendrocyte-lineage cells. The cells cultured using the method of the present invention can be passaged more than 6 times and expanded over 1,000 times while retaining their ability to subsequently differentiate into oligodendrocyte-lineage cells. In some embodiments, the expanded cell population resulting from the culture method of the present invention comprises or can differentiate into a population of cells having at least 30%, 50%, 70% or 80% oligodendrocyte-lineage cells of differentiated cells in serum-free culture condition. In a preferred embodiment, the expanded cell culture population resulting from the culture method of the present invention comprises at least 90% oligodendrocyte-lineage cells of differentiated cells. In preferred embodiments, the expanded cells are multipotent. In some embodiments the majority of expanded cells are capable of differentiating into oligodendrocyte-lineage cells upon culturing in decreased PDGF-AA medium (i.e., 20 ng/ml PDGF-AA, preferably with 10 ng/ml bFGF with or without 50 μM 1-thioglycerol and optionally with at least 10 ng/ml IGF-1) without replenishing bFGF between changing medium. In some embodiments the majority of expanded cells are capable of differentiating into oligodendrocyte-lineage cells upon culturing in 10 ng/ml of PDGF-AA, 100 ng/ml IGF-1, 100 μM pCPT-cAMP and 10 ng/ml BDNF in DMEM/F12 containing glutamine and HEPES and supplemented with B27 supplement, N2 supplement and 50 μM 1-thioglycerol.

The isolated mammalian neural stem cells and/or neural progenitor cells for use in the present invention may be obtained from the central nervous system of a mammalian, preferably a primate such as, but not limited to, a human. Oligodendrocyte progenitors and pre-progenitors are known to exist in white matter of the central nervous system. As such, suitable sources from which to isolate cells for use in the present invention include, but are not limited to, the optic nerve, corpus callosum and spinal cord. In addition, isolated stem cells may be derived from a mammalian fetus, preferably a primate fetus, such as but not limited to a human fetus, using methods known in the art. In some embodiments, the isolated stem cells are prepared from human fetal spinal cord tissue obtained from a human fetal spinal column. In a preferred embodiment, isolated cells for use in the present invention are obtained from 8-24 weeks gestational age, preferably 12-18 weeks gestational age human fetal spinal cord. Human fetal spinal columns can be obtained, for example, commercially through companies such as Advanced Bioscience Resources, Inc. (Alameda, Calif., USA) with the IRB permission and an informed consent from a donor. Spinal cord tissue can be dissected from the spinal column, with the meninges and peripheral nerves removed. The tissue then can be dissociated, washed and placed in a culture vessel containing a growth medium that permits cell proliferation.

Suitable culture vessels may include, but are not limited to, culture vessels with a culture surface having one or a combination of poly-amino acids (e.g., poly-lysine and/or poly-ornithine), tissue culture plastic and surfaces treated with laminin, vitronectin or fibronectin. Cells generally may be plated at a density ranging from $10^4$ to $10^5$ cells/cm$^2$, preferably at a density of approximately $3 \times 10^4$ to $5 \times 10^4$ cells/cm$^2$. Poly-omithine or poly-lysine may be used to coat culture vessels as reported previously (Raff et al, *J. Neurosci.*, 3:1289, 1983; Raff et al, *Nature.*, 303:390, 1983; Protocols for Neural Cell Culture, 3$^{rd}$ edition, Humana Press, Inc.). Culture vessels may be coated with 1 to 40 μg/ml of poly-ornithine, preferably 2 to 20 μg/ml, more preferably 5 to 15 μg/ml. The strength of cell attachment can vary depending on vendor, surface modification, format and specific lot of culture vessels. The optimal concentration of coating materials can be determined for each source of culture vessels using methods known in the art. In some embodiments a two-hour incubation with 10 μg/ml of poly-ornithine or poly-lysine is performed to coat vessels, for example, from BD Falcon (Sparks, Md., USA). In some embodiments a 30-minute incubation with 5 μg/ml of poly-ornithine or poly-lysine can be performed to coat vessels, for example, from Nalgen Nunc International (Rochester, N.Y., USA).

The isolated neural stem cells and/or neural progenitor cells obtained from a mammalian central nervous system are cultured in a serum-free chemically defined culture medium that permits cell expansion without promoting differentiation of the cells (for example, into neurons, astrocytes or oligodendrocytes). The culture medium comprises a base medium such as, but not limited to, Dulbecco's Modified Eagle Medium: Nutrient Mixture F-12. 1:1 (DMEM/F12) (Invitrogen®) (e.g., Iscove's Modified Dulbecco's Medium, RPMI-1640 and Neurobasal). The base medium may be supplemented with various components to support cell health and survival. Such components may include, but are not limited to, at least 0.25% non-essential amino acids [NEAA (Invitrogen®)-a 1% solution contains 100 µM of L-Alanine, L-Asparagine $H_2O$, L-Aspartic Acid, L-Glutamic Acid, Glycine, L-Proline, and L-Serine], at least 1.0 mM glutamine, at least 0.5 mM pyruvate, at least 1% B27 supplement (Invitrogen®), at least 0.1 mM N-acetyl-cysteine and/or at least 10 µM β-mercaptoethanol. In some embodiments the base medium may comprise NS21 (as disclosed in Y. Chen et al., *J. Neurosci. Methods.*, 171:239, 2008) in place of B27 supplement. B27 supplement contains bovine serum albumin, transferrin, insulin, progesterone, corticosterone, triiodo-l-thyronine, retinol acetate, DL tocopherol, DL tocopherol acetate, Biotin, Linoleic acid, Linolenic acid, ethanolamine, Na Selenite, L-carnitine, glutathione reduced, catalase, superoxide dismutase, D-galactose and putrescine. Invitrogen has disclosed its ingredients but hasn't disclosed their concentration. However, the concentration of each ingredients of their original formulation, B18 supplement, was disclosed. NS21 was developed based on this information and the concentration of each gradient was disclosed. It worked in neuronal culture as good as B27 supplement. In addition, NS21 could be used to culture neural stem cells and oligodendrocyte progenitors derived from human embryonic stem cells. Therefore, this supplement is thought to be a good candidate to replace B27 supplement. In a preferred embodiment, the culture medium comprises DMEM/F12 supplemented with 1-4 mM, more preferably 2.5 mM glutamine; 10-25 mM, more preferably 15 mM HEPES; 0.5-2.0 mM, more preferably 1 mM pyruvate; 1 to 4%, more preferably 2% B27 supplement; 0.25-3%, more preferably 1% NEAA; 1-200 µM, more preferably 50 µM 1-thioglycerol; 0.1-3 mM, more preferably 1 mM N-acetyl-cysteine; and/or 10-100 µM, more preferably 55 µM β-mercaptoethanol.

Furthermore, oxygen may facilitate differentiation of neural progenitor cells. Therefore, to reduce cell differentiation, the cells may be cultured in a 1-20% $O_2$ growth environment. In a preferred embodiment, the cells are cultured in a culture flask in an incubator providing a 37° C., 1-10%, more preferably 5% $O_2$, 5% $CO_2$ growth environment. After establishing HFSC cells, the effect of oxygen concentration was assessed but there was no increase of differentiated cells in 20% $O_2$ condition compared to 5% $O_2$ condition in the culture condition to expand HFSC cells. The growth of HFSC cells in 5% $O_2$ condition was a little bit faster than that in 20% $O_2$ condition. Oxygen is a cause of oxidative stress and known to induce mutation of p53 in rodent cells. To reduce a risk of mutation, we kept culturing HFSC cells in 5% $O_2$ condition.

The neural stem cells and/or neural progenitor cells are cultured in culture medium further comprising growth factors to stimulate proliferation for isolating the cells. The culture medium may contain at least 5, 10, 20 or 40 ng/ml platelet-derived growth factor-AA (PDGF-AA), at least 2.5, 5 or 10 ng/ml basic FGF (bFGF), and/or at least 10, 25 or 50 µM 1-thioglycerol to isolate the cells. In some embodiments the culture medium further comprises at least 1, 5 or 10 ng/ml insulin-like growth factor-1 (IGF-1). In some embodiments PDGF-AA may be replaced with PDGF-BB, PDGF-AB, PDGF-CC, or PDGF-DD. In some embodiments bFGF may be replaced with other member of fibroblast growth factors (e.g. FGF-4 or FGF-9). In some embodiments IGF-1 may be replaced with IGF-2. In a preferred embodiment, the culture medium comprises 40-60 µM 1-thioglycerol, 40-200 ng/ml PDGF-AA, 5-100 ng/ml bFGF, and 5-100 ng/ml IGF-1 to isolate the cells.

The isolated neural stem cells and/or neural progenitor cells are cultured in culture medium further comprising growth factors to stimulate proliferation after isolating the cells. The culture medium may contain at least 1, 2, or 5 ng/ml platelet-derived growth factor-AA (PDGF-AA), at least 0.5, 1 or 5 ng/ml basic FGF (bFGF), and/or at least 10, 25 or 50 µM 1-thioglycerol to expand the cells. In some embodiments the culture medium further comprises at least 1, 2 or 5 ng/ml insulin-like growth factor-1 (IGF-1). In a preferred embodiment, the culture medium comprises 40-60 µM 1-thioglycerol, 5-100 ng/ml PDGF-AA, 1-50 ng/ml bFGF, and 5-100 ng/ml IGF-1 to expand the cells after the isolation of HFSC cells.

The isolated neural stem cells and/or neural progenitor cells grown under culture conditions of the present invention exhibit a doubling time of 50-120 hours. In preferred embodiments, the doubling time is about 60 to 100 hours. The cells can continue this proliferation rate through at least 8, 11, 14 or 17 passages. The cells may be expanded at least 100, 250, or preferably at least 500 times per month. In preferred embodiments, the cells cultured using the method of the present invention exhibits an expansion rate >1 for more than 18 passages.

EXAMPLES

Example 1

HFSC Cell Culture and Expansion; Identification of Base Medium and Growth Factors Several medium and supplements were tested in a preliminary experiment using HFSC cells derived from human 12-week fetal spinal cord, which was obtained from Advanced Bioscience Resources, Inc. (Alamada, Calif., USA) with an informed consent of a donor. The cells were cultured in DMEM:F-12 (1:1) (DMEM/F12) (Invitrogen™, Carlsbad, Calif., USA) supplemented with 2 mM glutamine (Invitrogen™), 1 mM pyruvate (Invitrogen™) and 2% B27 supplement (Invitrogen™) initially. Various growth factors were examined whether they stimulate growth of HFSC cells. Most effective growth factors were the combination of PDGF-AA and bFGF. The cells could grow in the presence of PDGF-AA and bFGF but showed vacuoles and looked unhealthy. Several supplements were tested and it was observed that DMEM/F12 supplemented with 1% NEAA in addition to 2 mM glutamine, 1 mM pyruvate and 2% B27 supplement could decrease vacuoles and increase cell number slightly (data not shown). Other supplements including 1 mM N-acetyl-cysteine (Sigma-Aldrich™, St. Louis, Mo., USA) and 55 µM β-mercaptoethanol (Invitrogen™) seemed to improve the cells' status but the improvements were not as prominent as with NEAA (data not shown). Thus, DMEM/F12 supplemented with 2 mM glutamine, 1 mM pyruvate, 2% B27 supplement, 1% NEAA, 1 mM N-acetyl-cysteine and 55

μM β-mercaptoethanol was identified as optimal base medium and was used thereafter to culture HFSC cells.

Human 15-week fetal spinal cord was dissected from the spinal column, with the meninges and peripheral nerves removed. The tissue then was dissociated with Accutase and washed and cells obtained from human fetal spinal cord were placed in a culture vessel containing the following growth medium: DMEM/F12 containing 2.5 mM glutamine and 15 mM HEPES, 2% B27 supplement (Invitrogen™), 1% NEAA, 1.5 mM pyruvate (Invitrogen™), 55 μM β-mercaptoethanol (Invitrogen™), 1 mM N-acetyl-L-cysteine (Sigma-Aldrich™), 20 ng/ml PDGF-AA (R&D SYSTEMS™, Inc., Minneapolis, Minn., USA) and 10 ng/ml bFGF (R&D SYSTEMS™). Cells were then placed in an incubator maintained at 37° C., 5% $O_2$, and 5% $CO_2$. bFGF (10 ng/ml) was added daily to the culture medium. Medium was changed every 2-3 days during passage. Based on the preliminary experiments, growing cells were not so many in the presence of PDGF-AA and bFGF and many cells stopped proliferating or died within a few weeks. This result seemed to be reasonable because PDGF-Rα expressing cells are usually less than 5% of cells. To remove cells that are not responsive to PDGF-AA and bFGF, cells were cultured in an ultra-low adhesion culture plate (OWENS CORNING™ Inc., Corning, N.Y., USA). The cells that are responsive to PDGF-AA and bFGF made spheres (see FIG. 3, slide A) while cells that are not responsive to them did not form spheres. Spheres were collected at lower speed of centrifugation (300 rpm for collecting spheres vs. 1,000 rpm for collecting single cells) for medium change and passaging. After 9 days, cells were harvested and passaged onto poly-ornithine-coated culture vessels. After this period, cells were passaged every 7-14 days. The cells exhibited a heterogeneous morphology at these early stages (see FIG. 3, slides B and C) and many of the cells stopped proliferating within a month. The proliferation rate became slower over time and the cells eventually did not expand. In addition, the cells began to appear unhealthy, forming vacuoles in their cytoplasm.

Example 2

Identification of Optimal Growth Condition for HSCF Cell Expansion

As mentioned in Example 1, inclusion of PDGF-AA and bFGF in the culture medium supported adequate growth of the HFSC cells initially, but the proliferation rate slowed after 2 passages. NT-3 (R&D SYSTEMS™) and IGF-1 (Sigma-Aldrich™) were tested to determine if they could enhance the proliferation of HFSC cells. The presence of 20 ng/ml PDGF-AA with 10 ng/ml bFGF was insufficient to stimulate the proliferation rate of the cells (the expansion rate was <1) (see FIG. 4). Subsequent addition of 5 ng/ml NT-3 and/or 10 ng/ml IGF-1 resulted in an enhanced proliferation rate (the expansion rate became >1). Combination of NT-3 and IGF-1 was most effective at passage 3. The cells obtained from each condition were further passaged to confirm their effects. The cells were harvested earlier because the cells started forming spheres. At passage 4, the recovery of proliferation rate by combination of NT-3 and IGF-1 was decreased and single addition of IGF-1 became most effective at passage 4. Combination of NT-3 and IGF-1 might cause differentiation of cells or form more spheres and lost while changing medium. Thus, the addition of IGF-1 was identified as a most effective survival factor and was used thereafter to culture HFSC cells. However, the proliferation rate of the HFSC cells began to slow again at the end of passage 4 and the cell number was decreased comparing to the seeded cell number. Therefore, another supplement, 1-thioglycerol, was examined whether it could enhance the proliferation of HFSC cells at passage 5.

FIG. 5 shows the effect of 1-thioglycerol on the proliferation of HFSC cells. The initial growth factor combination (20 ng/ml PDGF-AA+10 ng/ml bFGF) couldn't expand cells at all (data was not shown in this figure because it was under the countable range). The growth factor combination used from passage 3 (20 ng/ml PDGF-AA+10 ng/ml bFGF+10 ng/ml IGF-1) was more effective than this combination (20 ng/ml PDGF-AA+10 ng/ml bFGF) but unable to stimulate HFSC cell proliferation well after passage 4 (FIG. 4). Many cofactors related to the biosynthesis and degradation of fatty acids and related long-chain hydrocarbons feature thiols. 1-thioglycerol was next tested on the HFSC cells since it is one of thiol-based antioxidants and has been reported to stimulate the proliferation of some cells (i.e. mouse embryonic cortical and hippocampal neurons, mouse bone marrow mast cells, and human B cell lines) in culture. In addition, higher dose of PDGF-AA (100 ng/ml) was also tested whether it could complement the decrease of reactivity to growth factors.

The addition of 50 μM 1-thioglycerol in the presence of 20 ng/ml PDGF-AA, 10 ng/ml bFGF and 10 ng/ml IGF-1 stimulated proliferation slightly but the cell number was still decreased (expansion rate <1). This result was similar to that obtained in the absence of 1-thioglycerol when the PDGF-AA concentration was increased to 100 ng/ml in the presence of 10 ng/ml bFGF+10 ng/ml IGF-1. However, when both 50 μM 1-thioglycerol and increased PDGF-AA (100 ng/ml) were included in the culture medium (along with 10 ng/ml bFGF and 10 ng/ml IGF-1), the two components appeared to work synergistically, significantly increasing the cell number (expansion rate >1). When IGF-1 was eliminated from this supplement cocktail (i.e. total supplementation was 100 ng/ml PDGF-AA+10 ng/ml bFGF+50 μM 1-thioglycerol), the expansion rate decreased to <1, indicating that IGF-1 also promoted HFSC cell proliferation and/or survival. However, if HFSC cells were cultured in this condition longer, HFSC cells might be expanded even in this condition. This data indicated that the addition of 50 μM 1-thioglycerol and the increase of PDGF-AA concentration to 100 ng/ml in addition to 10 ng/ml bFGF+10 ng/ml IGF-1 were important to expand the cells. Furthermore, addition of IGF-1 might not be mandatory but was still effective even in the presence of 50 μM 1-thioglycerol and 100 ng/ml PDGF-AA to increase the expansion rate. The combination of 50 μM 1-thioglycerol and 100 ng/ml PDGF-AA in addition to 10 ng/ml bFGF+10 ng/ml IGF-1 was used thereafter to culture HFSC cells.

The HFSC cells were further expanded in the presence of 100 ng/ml PDGF-AA, 10 ng/ml bFGF, 10 ng/ml IGF-1 and 50 μM 1-thioglycerol after passage 6. The cells began to proliferate more rapidly under these conditions after passage and were expanded 3-4 times within a week. The doubling time was approximately 60-100 hours in this condition. The HFSC cells were able to maintain this proliferative state even after passage 8 (see FIG. 3, slide D), passage 11 (see FIG. 3, slide E) and passage 19 (see FIG. 3, slide F). Thus, defined medium comprising 100 ng/ml PDGF-AA, 10 ng/ml bFGF, 10 ng/ml IGF-1 and 50 μM 1-thioglycerol was identified as the optimal culture condition for long term expansion of the neural stem cells and/or neural progenitor cells.

Example 3

Spontaneous Differentiation Technique of HSCF Cell

While testing various culture conditions, it was observed that when HFSC cells were cultured with the removal of bFGF from the medium, many of the cells seemed to differentiate into bipolar or multipolar cells (indicative of oligodendrocyte) and died soon. To avoid these cell death, a spontaneous differentiation technique was developed.

Culture medium was usually changed every 2 days for expanding HFSC cells and it was thought to be very important to keep HFSC cells in proliferative state. To enhance cell differentiation, medium was changed every 3 or 4 days for this experiment. Basic FGF and high concentration of PDGF-AA were thought to block differentiation of HFSC cells but they were also important for HFSC cells to survive. Therefore, PDGF-AA concentration was decreased from 100 to 20 ng/ml in the presence of 10 ng/ml bFGF, 10 ng/ml IGF-1 with 50 μM 1-thioglycerol or without 1-thioglycerol. HFSC cells couldn't survive well if bFGF was removed. Usually, bFGF were replenished everyday to keep HFSC cells in proliferative state. When replenishing bFGF was stopped, many HFSC cells separated from their clusters and formed complex web-like processes (indicative of pro-oligodendroblasts and/or immature oligodendrocytes) and survived well as shown in FIG. 7, slides A and B.

These process-bearing cells with spider's web-like morphology were positive for O4 antigen and/or GalC antigen as shown in FIG. 7, slides C-F, therefore, they were thought to be pro-oligodendroblast (O4-positive and GalC-negative) or immature oligodendrocyte (O4-positive and GalC-positive). Even in the presence of 1-thioglycerol, HFSC cells could be differentiated but complexity of process looked simpler when 1-thioglycerol was present in the culture medium as shown in FIG. 7, slides A & B. In addition, other cell types (e.g., astrocyte and neuron) were rarely observed and HFSC cells were thought to be prone to differentiate into only oligodendrocyte-lineage cells. This technique enabled to observe differentiated oligodendrocyte-lineage cells in a healthy state.

These data further indicate that the culture conditions of the present invention are particularly useful for expanding isolated neural stem cells and/or neural progenitor cells that are prone to differentiate into oligodendrocytes, since most of the differentiated cells exhibited oligodendrocyte characteristics and resemble oligodendrocytes or pro-oligodendrocytes.

Example 4

Induction of HFSC Cell from Conventional Neural Stem Cell

As shown in FIG. 1, conventional neural stem cell is thought to be a predecessor of HFSC cell. To confirm this relationship, it was examined whether HFSC cell could be induced from conventional neural stem cell that was reported previously. The cells from a second tissue sample of human fetal spinal cord (11 weeks gestation) were initially cultured in the presence of 10 ng/ml EGF and 10 ng/ml bFGF in DMEM/F12 containing 2.5 mM glutamine, 15 mM HEPES, 2% B27 supplement, 1% NEAA, 1.5 mM pyruvate. 55 μM β-mercaptoethanol, and 1 mM N-acetyl-L-cysteine for 15 days to expand conventional neural stem cells. Many different cell types were present initially but some expandable cell population was obtained at the end of the primary culture. These results are illustrated in FIG. 8, slide A at Day 15 of Passage 0. After the first passage the cells were cultured in the same condition as cell line #2b (i.e. HFSCM1 medium with 10 ng/ml bFGF, 10 ng/ml IGF-1, 100 ng/ml PDGF-AA and 50 μM 1-thioglycerol) through 15 passages.

The morphology of the cells from the expandable cell population obtained at the end of the primary culture became homogenous at around passage 5 and the cells tended to form clusters and spheres, similar to those that formed with cell line #2b (see FIG. 8, slides B-F). In addition, this cell line could differentiate into oligodendrocyte-lineage cells spontaneously (data not shown), showed the same immune-phenotype as cell line #2b (data not shown) and the same marker expression pattern by flow cytometry as described in Example 7. The cells from this cell line were frozen down for future testing (e.g. FIG. 12). This data suggests that HFSC cell could be induced from conventional neural stem cell and that conventional neural stem cell is thought to be a predecessor of HFSC cell.

PDGF-AA was thought to work through PDGF receptor a. This receptor is known to be stimulated by all PDGF family members (PDGF-AA, PDGF-BB, PDGF-AB, PDGF-CC and PDGF-DD). PDGF-BB was used to examine whether PDGF-BB could replace PDGF-AA using HFSC cell cell line #2b and cell line #3. PDGF-BB could expand both cell lines in the same condition except for PDGF-AA and it was proved that PDGF-AA could be successfully replaced with other PDGF family members.

Example 5

Confirmation of Optimal Cell Culture Components

While the inventor tested various culture conditions after HFSC cell (cell line #2b) was established, the inventor noticed that dose response for each growth factor has been changed. To isolate HFSC cell (cell line #2b), higher concentration of PDGF-AA (100 ng/ml) was necessary in addition to 50 μM 1-thioglycerol. After this cell line became proliferate constantly, higher concentration of PDGF-AA (100 ng/ml) was no more required to expand this cell line. Expansion rate was saturated at around 10-20 ng/ml of PDGF-AA and higher concentration of PDGF-AA (100 ng/ml) had no additional effects on their growth. This may be because of a long-term culture or a continuous usage of 1-thioglycerol. To establish cell line #2b and cell line #3 of HFSC cells, 1-thioglycerol was used after several passages. To examine the effect of higher concentration of PDGF-AA, new cell lines were established in the presence of 1-thioglycerol from an initial culture. In addition, the response to bFGF and IGF-1 seemed to be saturated at 20 ng/ml and 40 ng/ml, respectively. When higher concentration of IGF-1 (50-500 ng/ml) was used, more differentiated cells could be seen (it looked like around 1%). Therefore, 20 ng/ml IGF-1 was considered to be preferable to expand HFSC cells. The usage of 20 ng/ml bFGF and 20 ng/ml IGF-1 improved the expansion rate 5-10% compared to the usage of 10 ng/ml bFGF and 10 ng/ml IGF-1. Therefore, 20 ng/ml bFGF and 20 ng/ml IGF-1 were used for this experiment.

HFSC cells from a third sample (12 weeks gestation) were cultured to see if higher concentration of PDGF-AA is required in the identified optimal culture medium components and if they would provide similar growth characteristics in another batch of cells. The cells were cultured in the same culture medium as cell line #2b and #3 (i.e. HFSCM1 medium and 50 μM 1-thioglycerol) with 20 ng/ml (cell line #4A) or 100 ng/ml (cell line #4B) PDGF-AA in addition to 20 ng/ml bFGF and 20 ng/ml IGF-1. At the end of the first passage, cell number of cell line #4A was less than one third of that of cell line #4B (see FIG. 11, slide A and slide B). However, cell line #4A started to proliferate at the similar speed as cell line #4B after passage 1 even with lower PDGF-AA concentration than cell line #4B. The morphology of the cells became homogenous at passage 3 and the cells tended to form clusters and spheres, similar to those that formed with cell line #2b or #3 (see FIG. 10, slides C-F). In addition, these cells could differentiate into oligodendrocyte-lineage cells spontaneously as cell line #2b and #3 did. This result suggested that higher concentration of PDGF-AA was not mandatory but preferable to isolate HFSC cells and that higher concentration of PDGF-AA was not necessary once HFSC cells were established. Furthermore, this culture method could provide similar growth characteristics in another batch of cells and it was confirmed that this process could be repeatable. The cells from this cell line were frozen down for future testing.

Example 6

Ability of Expanded HFSC Cells to Recover and Grow after Freeze-Thaw Cycle

The cells of cell line #2b were cryopreserved in the presence of 8% DMSO at passage 10, 11 and 12. The HFSC cells (cell line #2b) frozen at passage 11 have been deposited at ATCC (accession number PTA-12291). The cells of cell line #3 were also cryopreserved in the presence of 8% DMSO at passage 9 and 10. The cells of cell line #4A and #4B grew faster than cell line #2b or #3, therefore they were cryopreserved in the presence of 8% DMSO at passage 4 and 5 (cell line #4A) or passage 3, 4 and 5 (cell line #4B) in the same condition. The same medium to culture the HFSC cell (HF-SCM1 medium and 50 μM 1-thioglycerol) was used for freezing the HFSC cells. The cells were later thawed and cultured in the above described serum-free HFSCM1 medium and 50 μM 1-thioglycerol with 10 ng/ml bFGF, 10 ng/ml IGF-1, 100 ng/ml PDGF-AA or 20 ng/ml bFGF. 20 ng/ml IGF-1, 20 ng/ml PDGF-AA. These cells were observed to proliferate at a similar rate as before freezing (see FIG. 6, FIG. 9 and FIG. 11). The frozen cells were used for later experiments shown in FIGS. 12-15.

Example 7

Characterization of Expanded and Undifferentiated HFSC Cells

When the HFSC cells of Example 2 were cultured in the presence of 100 ng/ml PDGF-AA, 10 ng/ml bFGF, 10 ng/ml IGF-1 and 50 μM 1-thioglycerol, they grew in clusters and/or spheres as shown in FIG. 3, slides D-F. The scattered cells that separated from the clusters tended to differentiate into oligodendrocytes as shown in FIG. 3, slides D and E. Even when the cells were passaged in a single cell state, they eventually began to gather and form clusters again. Their shape in this proliferative state resembled oligodendrocyte pre-progenitor cells (see Ben-Hur et al, *J. Neurosci.*, 18:5777, 1998: Gago et al, *Mol. Cell. Neurosci.*, 22:162, 2003), but not like O-2A progenitors which grow in a bipolar morphology without forming any clusters. Even rat oligodendrocyte pre-progenitor cells were reported a long time ago, the human counterpart has not been reported. However, it was unnecessary to identify the precise stage of oligodendrocyte predecessor cell in the expanded cell culture since they retained their ability to differentiate into oligodendrocytes (as shown below) regardless.

In order to characterize the immuno-phenotype of the undifferentiated HFSC cells, the cells at passage 11-15 were dissociated into a single cell state with Accutase (Innovative Cell Technologies, San Diego, Calif., USA) and grown in poly-ornithine-coated 24-well culture plates and cultured for 3-7 days in the presence of 100 ng/ml PDGF-AA, 10 ng/ml bFGF, 10 ng/ml IGF-1 and 50 μM 1-thioglycerol. The cells were then fixed with 4% paraformaldehyde and then washed with PBS. For staining surface antigens like CD133, PDGF-Rα, NG2, A2B5, O4, O1, GalC and PSA-NCAM, cells were blocked with PBS containing 3% normal gout serum (NGS) and stained with antibodies. For staining intracellular antigens like Sox2, nestin, Olig2, myelin basic protein (MBP), Vimentin, GFAP, βIII Tublin, Neurofilament-L and MAP2, cells were permeabilized with 0.1% Triton X-100 in ice-cold PBS for 10 min before blocking. CD133/1 mouse IgG1 monoclonal antibody (Clone AC133, Miltenyi Biotec), anti-PDGF-Rα rabbit polyclonal antibody (Upstate), anti-NG2 rabbit polyclonal antibody (Millipore®), anti-PSA-NCAM mouse IgM monoclonal antibody (Millipore®), A2B5 mouse IgM monoclonal antibody (Millipore®), O4 mouse IgM monoclonal antibody (R&D SYSTEMS™), O1 mouse IgM monoclonal antibody (Millipore®), anti-Sox2 rabbit polyclonal antibody (Millipore®), anti-Nestin mouse IgG1 monoclonal antibody (Millipore®), anti-Olig2 mouse monoclonal IgG2a antibody, anti-GalC monoclonal IgG3 antibody (Millipore®), anti-MBP rat monoclonal IgG2a antibody (Millipore®), anti-Vimentin mouse IgG1 monoclonal antibody (Santa Cruz), anti-GFAP rabbit polyclonal antibody (Millipore®), anti-βIII Tublin monoclonal mouse IgG1 antibody (Millipore®), anti-Neurofilament-L mouse monoclonal IgG1 antibody (CELL SIGNALING TECHNOLOGY®), anti-MAP2 rabbit polyclonal antibody (Millipore®) and anti-MAP2 mouse IgG1 monoclonal antibody (Millipore®) were used at 1:300 (CD133/1), 1:300 (PDGF-Rα), 1:600 (NG2), 1:1000 (PSA-NCAM), 1:1000 (A2B5), 1:1000 (O4), 1:1000 (O1). 1:1000 (Sox2), 1:200 (Nestin), 1:200 (Olig2), 1:100 (GalC), 1:50 (MBP), 1:500 (Vimentin), 1:1000 (GFAP), 1:100 (βIII Tublin), 1:200 (Neurofilament-L), 1:1000 (MAP2, polyclonal) or 1:200 (MAP2, monoclonal) in PBS containing 3% NGS. After overnight incubation at 4° C., wells were washed with 3 changes of PBS containing 3% NGS. In some case, a live cell staining for some cell surface antigen (NG2, A2B5, O4, O1 and GD3) was used to reduce non-specific signals. In such case, cells were stained with each primary antibody before fixation without blocking. Anti-NG2 rabbit polyclonal antibody. A2B5 mouse IgM monoclonal antibody, O4 mouse IgM monoclonal antibody, O1 mouse IgM monoclonal antibody, and anti-Disialoganglioside GD3 mouse monoclonal IgG3 antibody (Millipore®) were used at 1:150 (NG2), 1:100 (A2B5), 1:200 (O4), 1:100 (O1) and 1:200 (GD3) in PBS containing 0.5% BSA. After 30 minutes incubation at room temperature, wells were washed with 3 changes of PBS containing 0.5% BSA. The secondary antibodies, DYLIGHT™ 488-conjugated AffiniPure Goat anti-rabbit IgG (Fcγ Fragment specific), DYLIGHT™ 488-conjugated AffiniPure Goat anti-mouse IgG (Fcγ Fragment specific), DYLIGHT™ 488-conjugated AffiniPure Goat anti-rabbit IgG (H+L), DYLIGHT™ 488-conjugated AffiniPure Goat anti-rat IgG (H+L), DYLIGHT™ 594-conjugated AffiniPure Goat anti-mouse IgG (H+L), and/or DYLIGHT™ 594-conjugated AffiniPure Goat anti-mouse IgM (μ chain specific) (all secondary antibodies were purchased from Jackson ImmunoResearch Laboratories, Inc.) were used at dilution of 1:500 for 1 hour at room temperature. The cells were then washed with 2 changes of PBS. DAPI was used to counterstain cell nuclei. The cells were then observed using an Olympus IX81 equipped for epifluorescence.

Most of the HFSC cells were CD133-positive (see FIG. 12, slide A & B), Sox2-positive (see FIG. 12, slides C & D) and nestin-positive (see FIG. 12, slide E & F), indicative of neural stem cells. Most of the HFSC cells were Olig2-positive (often indicative of progenitor cells for motor neuron and oligodendrocyte) (see FIG. 12, slides G & H), PDGF-Rα-positive (often indicative of oligodendrocyte-lineage cells) (see FIG. 12, slides I & J), A2B5-positive (A2B5 is usually absent from neural stem cells and found on glial progenitor cells, oligodendrocyte progenitor cells and type-2 astrocytes) (see FIG. 12, slides M & N), indicative of oligodendrocyte progenitor cells. Most of the HFSC cells were PSA-NCAM-positive (see FIG. 12, slides O & P) but there were variety in their expression levels (PSA-NCAM is usually absent from neural stem cells and found on neuronal progenitor cells and oligodendrocyte pre-progenitor cells). No GFAP-positive cells could be seen while most of them were vimentin-positive (see FIG. 12, slide Q-S). At least 90% of HFSC cell seemed to be positive for above markers except for GFAP but the precise counting was very difficult because HFSC cell tended to make clusters and to be detached from culture vessels very easily during fixation and staining. To quantify their purity, a flow cytometry analysis was done and shown in FIG. 13.

In addition, undifferentiated HFSC cells were weakly stained with O4 antibody that is a marker for pro-oligodendroblast (O4-positive, GalC-negative) and immature oligodendrocyte (O4-positive, GalC-positive) by immunocytochemistry but it was difficult to distinguish with weak staining and non-specific staining. Some pro-oligodendroblast which shows strong O4-positive cells with multipolar morphology could be seen in this culture but their frequency of appearance was less than 1% of total cells.

In addition, undifferentiated HFSC cells were weakly stained with anti-MAP2 antibody but their morphology was not like neuron. When the antibody was used with the cells differentiated in the presence of serum, neuron was identified with strong signals and neuronal morphology (see FIG. 14, slide H). Such strong signal of MAP2 with neuronal morphology was not identified in undifferentiated HFSC cells. This weak signal disappeared when the cells were differentiated, so that this staining seemed to be specific and undifferentiated HFSC cells might not be non-specific staining.

Overall, HFSC cell expressed specific markers for neural stem cell (CD133, Sox2, and Nestin) and specific markers for oligodendrocyte-lineage cells (Olig2, NG2, A2B5, and O4). These data suggested that HFSC cell might be an intermediate cell between neural stem cell and oligodendrocyte progenitor cell. Furthermore, HFSC cell expressed PSA-NCAM in addition above antigens, indicative to be the human counterpart of rat oligodendrocyte pre-progenitor cell.

Polysialic acid (PSA) of PSA-NCAM is a long, negatively charged, cell-surface glycan with an enormous hydrated volume that serves to modulate the distance between cells. PSA is involved in a number of plasticity-related responses in the adult CNS, including changes in circadian and hormonal patterns, adaptations to pain and stress, and aspects of learning and memory (Rutishauser *Nat. Rev. Neurosci.*, 9:26, 2008). One of the roles of PSA in the neonatal nervous system is in the migration of oligodendrocyte progenitors. When PSA is removed from migrating O2A progenitors, migration of O2A progenitor was inhibited in wound model (Barral-Moran et al, *J. Neurosci. Res.*, 72:679, 2003). Another role is controlling differentiation timing of cells. PSA is expressed on both developing axons and oligodendrocyte precursors, and its down regulation on these cells correlates with the onset of myelination. PSA is also related plasticity-associated responses of the adult CNS. Given the ability of PSA to regulate developmental and adult plasticity, it follows that PSA-expressing cell could have the therapeutic value in situation in which tissues have been damaged by injury or disease. Axonal regrowth in the PSA-expressing region (engineered PSA expression in the scar or on grafted Schwann cells) were observed through the scar in trauma model. HFSC cell is an endogenous PSA-expressing cell and will have the same effect on treating the trauma like brain injury or spinal cord injury.

To further characterize the HFSC cells (cell line #2b), cells that were frozen at passage 11 were thawed, cultured in the growing condition described above and passaged every 7-9 days. The cells cultured for 9 days at passage 13 were then subjected to flow cytometry using the following antibodies: PE-conjugated anti-CD133/1 mouse IgG1 monoclonal antibody (Clone AC133, Miltenyi Biotec); PE-conjugated CD140a mouse IgG2a monoclonal antibody (Clone αR1, BD Pharmingen); PE-conjugated CD9 mouse IgG1 monoclonal antibody (Clone M-L13, BD Pharmingen); PE-conjugated CD44 mouse IgG2b monoclonal antibody (Clone G44-26, BD Pharmingen); PE-conjugated anti-PSA-NCAM mouse IgM monoclonal antibody (2-2B, Miltenyi Biotec); PE-conjugated A2B5 mouse IgM monoclonal antibody (Clone 105HB29, Miltenyi Biotec); PE-conjugated O4 mouse IgM monoclonal antibody (Clone O4, Miltenyi Biotec); and PE-conjugated anti-NG2 mouse IgG1 monoclonal antibody (R&D SYSTEMS™). Briefly, after dissociation with Accutase, the cells were washed and resuspended in ice-cold PBS with 2 mM EDTA and 0.5% BSA and kept on ice. After cell number was counted and cell number was adjusted to $1 \times 10^7$ cells/ml using ice-cold PBS with 2 mM EDTA and 0.5% BSA. 25 µl of cell suspension (250,000 cells) was transferred into each 1.5-ml tube. Primary antibodies then were added into each tube following the manufacturer's recommendation. PE-conjugated isotype controls for each antibody were used to set appropriate gates. After 20-min incubation on ice, cells were washed with ice-cold PBS with 2 mM EDTA and 0.5% BSA and resuspended in fixation buffer (BD Bioscience). After 20 minutes fixation on ice, cells were washed and resuspended in ice-cold PBS with 2 mM EDTA and 0.5% BSA. Fluorescence of cells was measured using FACS Canto II (BD Bioscience) and each data was analyzed using Gatelogic software (Inivai Technologies Pty Ltd.).

As show in FIG. 13, all or most of the HFSC cells (cell line #2b) were CD133-positive (100% of cells), CD9-positive (100% of cells), CD140a-positive (98.8% of cells), NG2-positive (89.8% of cells), A2B5-positive (99.9% of cells), O4-positive (94.6% of cells), PSA-NCAM-positive (68.9% of cells), and CD44-negative (0.4% of cells were positive). By immunocytochemistry, the O4 signal could be hardly distinguished from non-specific staining and was much weaker than the O4 signal of pro-oligodendroblasts or oligodendrocytes. From the result of flow cytometry, the O4 signal of HFSC cells (cell line #2b) could be separated from isotype control and HFSC cells (cell line #2b) appeared weakly positive for O4 antigen. HFSC cells (cell line #3) showed almost the same phenotype by flow cytometry. They were CD133-positive (98.4% of cells), CD9-positive (99.4% of cells), CD140α-positive (91.5% of cells), NG2-positive (63.4% of cells), A2B5-positive (99.8% of cells), O4-positive (71.6% of cells), PSA-NCAM-positive (74.7% of cells), and CD44-negative (0.3% of cells were positive).

Example 8

Differentiation Potential of Expanded HFSC Cells in Serum-Containing Medium

To test the differentiation potential of the expanded cells, the HFSC cells (cell line #3) were passaged to separate/single cell stage and cultured in serum-containing medium [Oligodendrocyte Precursor Cell Differentiation Medium (OPCDM)](ScienCell™ Research Laboratories) to stimulate differentiation. The cells were then stained with antibodies that recognize neurons (anti-βIII Tublin antibody, anti-Neurofilament-L antibody and anti-MAP2 antibody), oligodendrocyte progenitor cells and oligodendrocytes [O4 antibody, O1 antibody, anti-GalC antibody and anti-myelin basic protein (MBP) antibody], and astrocytes (anti-GFAP antibody) followed by a fluorescent dye-conjugated secondary antibody (DYLIGHT™ 488 or DYLIGHT™ 594, Jackson ImmunoResearch). DAPI was used to counterstain cell nuclei.

All three major central nervous system (CNS) phenotypes were observed following treatments to stimulate differentiation of HFSC cells. When the HFSC cells were cultured in serum-containing medium, βIII Tublin-positive cells, Neurofilament-L-positive cells, and MAP-2-positive cells were detected (indicative of neurons). There were many βIII Tublin-positive cells (FIG. 14, slide B) whereas small number of cells was positive for Neurofilament-L (FIG. 14, slide E) or MAP2 (FIG. 14, slide H). This result indicated many of them are immature neurons. HFSC cells could also differentiate into MBP-positive cells. MBP is a major component of myelin and expressed only in mature oligodendrocyte. This data indicates that HFSC cells have an ability to differentiate into mature oligodendrocytes. Co-localization of MBP and above neuronal markers was evaluated but only a few co-localization could be seen (FIG. 14, slides C, F, I). This might be due to immaturity of neurons because myelin will not be wrapped on axon of immature neuron. Co-localization of MBP and O4 antigen was also evaluated (FIG. 14, slides J-L). Most signal of MBP co-localized with signal of O4 antigen but only half of signal of O4 antigen co-localized with signal of MBP. This result was reasonable because O4 antigen is expressed in oligodendrocyte progenitors, immature oligodendrocytes and mature oligodendrocytes while MBP is expressed only in mature oligodendrocyte. These cells were also positive for GalC antigen that is a marker for immature oligodendrocytes (data not shown). GFAP-positive cells (astrocytes) and vimentin-positive cells were also detected as shown in FIG. 14, slides M-O. These data indicate that the expanded HFSC cells are multipotent and that, therefore, they are likely neural stem cells, since they are capable of giving rise to the three major central nervous system cell phenotypes depending on the environment. The HFSC cell (cell line #2b) was also tested in the same condition and showed the same multipotency as the HFSC cell did (cell line #3).

Example 9

Differentiation Potential of Expanded HFSC Cells in Serum-Free Medium

HFSC cells showed good differentiation potency into oligodendrocyte by reducing PDGF-AA concentration without replenishing bFGF as shown in FIG. 5. However, the differentiated cells were less than half of total cells. If HFSC cells were seeded at very low density (<0.5×10$^4$ cells/cm$^2$) without bFGF with 10 ng/ml of PDGF-AA and 100 ng/ml IGF-1, most cells seemed to differentiate but they were lost within a day. To examine their potency to differentiate into oligodendrocyte further, an induction of differentiation and a long-term cell survival were thought to be very important. Cyclic AMP (cAMP) is known to induce differentiation of many cell types. pCPT-cAMP which is a cell-permeable analog of cAMP was tested whether it could induce differentiation in HFSC cells. 100 µM pCPT-cAMP could induce differentiation of HFSC cells at high density (3×10$^4$ cells/cm$^2$) but cell couldn't survive well even in the presence of 100 ng/ml IGF-1. BDNF is reported to enhance differentiation of oligodendrocyte progenitors and support cell survival of differentiated cells. When HFSC cells were differentiated in the presence of 10 ng/ml of PDGF-AA, 100 ng/ml IGF-1, 100 µM pCPT-cAMP and 10 ng/ml BDNF in DMEM/F12 containing glutamine and HEPES and supplemented with B27 supplement, N2 supplement and 50 µM 1-thioglycerol, at least more than half of HFSC cells were differentiated into process-bearing cells. Because HFSC cell expresses several oligodendrocyte markers like O4 or NG2, the new method to distinguish HFSC cell and oligodendrocyte-lineage cell was required. Based on several trials, the inventor noticed that undifferentiated cells express GD3 stronger than oligodendrocyte progenitor cells and O4 vice versa (arrowhead of FIG. 11, slide A, slide B and slide C). When the cells were stained with GD3 and O4, oligodendrocytes could be distinguished using their staining pattern and their morphology. In addition, other cell types like neuron or astrocyte also could be identified because they don't express GD3 or O4 antigen. FIG. 15, slide D shows the ratio of each cell type. Undifferentiated cells were 23.5%±2.0% of total cells. Oligodendrocyte progenitor cells were 75.8%±2.1% of total cells. The other cell types were only 0.9%±0.6%. As mentioned above, the ratio of oligodendrocyte progenitor cells to differentiated cells (oligodendrocyte progenitor cells plus other cell types) were 99.1%±0.56% of differentiated cells whereas other cell types were 0.9%±0.56% of differentiated cells. This data indicates that HFSC cell has the high potential to differentiate into oligodendrocyte-lineage cells.

Example 10

HFSC Cell is Enriched or Selected by a Fluorescent Activated Cell Sorting (FACS) Method or a Magnetic Sorting Method The present invention disclosed the phenotype of HFSC cell that is CD133-positive, CD140a-positive, CD9-positive, CD44-negative, PSA-NCAM-positive, A2B5-positive, O4-positive, and NG2-positive. This information enables to select or enrich HFSC cell without culturing. CD133 is a marker for neural stem cell and not expressed in progenitor or precursor cells. CD9 is also used as a marker for neural stem cell but some oligodendrocytes are known to express CD9. PSA-NCAM and A2B5 are used to detect neuronal-restricted precursor or glial-restricted precursor. Most neural precursors and progenitors are thought to express PSA-NCAM and A2B5 or either PSA-NCAM or A2B5, their usage cannot enrich HFSC cell so well, especially in the first and second trimester. CD140a, NG2, A2B5 and O4 are used as markers for oligodendrocyte precursor cell, pro-oligodendroglia and oligodendrocyte. The expression level of CD140a and NG2 were higher in HFSC cell than oligodendrocyte precursor cell, pro-oligodendroglia or oligodendrocyte, whereas the expression level of A2B5 and O4 were lower in HFSC cell than oligodendrocyte precursor cell, pro-oligodendroglia or oligodendrocyte. The usage of CD140a and NG2 are thought to be more appropriate to enrich HFSC cell. Based on above information and the data described in this invention, the effectiveness of each marker to enrich HFSC cell will be CD140a>NG2>CD9>CD133>A2B5>O4, PSA-NCAM but this order will be vary depend on their gestation week.

However, a single marker will not be enough to select HFSC cells and combination of 2 markers can select HFSC cell more specifically. The combination of one of neural stem cell markers (CD133 or CD9) and one of oligodendrocyte-lineage markers (CD140a, NG2) will be very effective to select HFSC cells. Based on above knowledge, the most efficient combinations of markers to select the HFSC cells will be CD133 and CD140a among these combinations but other combinations should be also more effective than selection with a single marker.

The frequency of appearance of CD133 or CD140a is usually low (less than 5%) and the appearance of CD140a is later (expression starts from around 8-week and maximum at around 18-week of gestation week) than that of CD133. Therefore, the cells expressing both CD133 and CD140a will be very low (less than 1% of total cells) depending on their gestation week. Most of CD133-positive cells may not express CD140a if cells are derived from human fetal tissue at gestation week 15 or earlier. Because CD133-positive and CD140a-negative cell will express CD140a later, the HFSC cell can be obtained when the cells are cultured in the same condition for HFSC cells after the initial enrichment of CD133-positive cell.

The cell line #2b was deposited on Nov. 30, 2011, with Accession number PTA-12291 in the depository American Type Culture Collection (ATCC®), 10801 University Boulevard, Manassas Va. 20110 USA. The deposit is named Human neural stem cell: HFSC #2b.

I claim:

1. An enriched population of expanded human neural cells wherein the cells are progenitor cells or stem cells,
   wherein the cells have been cultured under conditions effective to enrich for the expanded neural cells, said conditions comprising, a culture medium comprising an effective amount of a growth supplement,
   wherein the growth supplement is 1-thioglycerol and the effective amount of growth supplement in the culture medium is at least 10 µM of 1-thioglycerol to isolate human fetal spinal cord ("HFSC") cells,
   wherein the cells maintain their capability to differentiate into neurons, astrocytes, and oligodendrocytes,
   wherein the cells maintain their ability to differentiate into oligodendrocyte lineage cells efficiently throughout subsequent passages, and wherein the population of cells express at least cell surface antigens CD133, CD140a, A2B5 and PSA-NCAM, and
   wherein at least about 90% of cells of the enriched population of expanded cells express the cell surface antigen CD133, CD140a, and A2B5, and at least about 60% of the enriched population of expanded cells also express the cell surface antigen PSA-NCAM.

2. The enriched population of expanded human neural cells of claim 1, wherein said cells have been deposited as ATCC accession number PTA-12291.

3. The enriched population of expanded human neural cells of claim 1, wherein the cells are derived from a human fetal neural tissue selected from the group consisting of spinal cord, cerebral cortex, hippocampus, striatum, basal forebrain, ventral mesencephalon, locus ceruleus, hypothalamus, cerebellum, corpus callosum and optic nerve.

4. The enriched population of expanded human neural cells of claim 3, wherein said neural tissue is isolated from the human spinal cord at 8-24 weeks gestation.

5. The enriched population of expand human neural cells of claim 1, wherein the conditions effective to enrich for the expanded neural cells further comprise two growth factors, and one survival factor.

6. The enriched population of expanded human neural cells of claim 5, wherein said two growth factors are platelet derived growth factor (PDGF) and basic fibroblast growth factor (bFGF) and are present in a concentration of at least 5 ng/ml of PDGF and at least 2.5 ng/ml of bFGF to isolate HFSC cells.

7. The enriched population of expanded human neural cells of claim 5, wherein said two growth factors are PDGF and bFGF and are present in a concentration of about 40 ng/ml to about 200 ng/ml of PDGF and about 5 ng/ml to about 40 ng/ml of bFGF to isolate HFSC cells.

8. The enriched population of expanded human neural cells of claim 5, wherein said two growth factors are PDGF and bFGF and are present in a concentration of about 100 ng/ml of PDGF and about 20 ng/ml of bFGF to isolate HFSC.

9. The enriched population of expanded human neural cells of claim 5, wherein said two growth factors are PDGF and bFGF and are present in a concentration of at least 1 ng/ml of PDGF and at least 0.5 ng/ml of bFGF to expand HFSC cells after a cell line is established and in order to maintain the cells.

10. The enriched population of expanded human neural cells of claim 5, wherein said two growth factors are PDGF and bFGF and are present in a concentration of about 5 ng/ml to about 100 ng/ml of PDGF and about 1 ng/ml to about 50 ng/ml of bFGF to expand HFSC cells after the establishment.

11. The enriched population of expanded human neural cells of claim 5, wherein said two growth factors are PDGF and bFGF and are present in a concentration of about 20 ng/ml of PDGF and about 20 ng/ml of bFGF to expand HFSC cells after the establishment.

12. The enriched population of expanded human neural cells of claim 5, wherein said one survival factor is Insulin-like growth factor (IGF) and is present in a concentration of at least 1 ng/ml of IGF.

13. The enriched population of expanded human neural cells of claim 5, wherein said one survival factor is IGF and is present in a concentration of about 5 ng/ml to about 100 ng/ml of IGF.

14. The enriched population of expanded human neural cells of claim 5, wherein said one survival factor is IGF and is present in a concentration of about 20 ng/ml of IGF.

15. The enriched population of expanded human neural cells of claim 1, wherein the cells can be frozen and thawed without losing its ability to differentiate into neurons, astrocytes, and oligodendrocytes throughout subsequent passages, and their ability to express at least cell surface antigens CD133, CD140a, A2B5 and PSA-NCAM.

16. A pharmaceutical neural stem cell composition comprising an enriched population of expanded human neural cells as in claim 1.

17. A method of treating a condition caused by a loss of myelin or a loss of oligodendrocytes comprising: administering to a subject the pharmaceutical composition of claim 16.

18. A pharmaceutical neural cell composition comprising the expanded neural cells of claim 1 that have been in vitro cultured.

19. A method of treating a condition caused by a loss of myelin or a loss of oligodendrocytes comprising: administering to a subject a therapeutically effective amount of a composition comprising the isolated expandable human neural cell of claim 1.

20. The method of claim 19, wherein said condition is a demyelinating disease or a neurodegenerative disease.

21. The method of claim 20, wherein said demyelinating disease is selected from the group consisting of spinal cord injury (SCI), multiple sclerosis (MS), hereditary leukodystrophy, transverse myelopathy/myelitis, progressive multiple focal leukoencephalopathy and other congenital demyelinating diseases.

22. The method of claim 20, wherein said neurodegenerative disease is selected from the group consisting of Alzheimer's disease, senile dementia of Alzheimer type (SDAT), Parkinson's disease, Huntington's disease, Amyotrophic Lateral Sclerosis (ALS), ischemia, blindness and a neurodegenerative disease caused by injury to myelinated neurons.

23. The method of claim 20, wherein the administering step comprises injecting the expandable human neural cell into neural tissue or lateral ventricles affected by the demyelinating disease or the neurodegenerative disease.

24. The method of claim 23, wherein said neural tissue is selected from the group consisting of the spinal cord, the subventricular zone, the corpus callosum, the cerebellum, the basal ganglia, the nucleus basalis and the substantial nigra.

25. The method of claim 20, wherein the administering step comprises injecting the expandable human neural cells into said subject by the method consisting of transuterine fetal intraventricular injection, intraventricular injection, intraparenchymal injections, intravitreal injection and intravascular administration.

26. The method of claim 20, further comprising the step of differentiating the expandable human neural cell prior to the administering step.

\* \* \* \* \*